(12) United States Patent
Miles et al.

(10) Patent No.: US 7,560,869 B2
(45) Date of Patent: Jul. 14, 2009

(54) METHOD AND APPARATUS FOR REMOTELY MONITORING PROPERTIES OF GASES AND PLASMAS

(75) Inventors: Richard B. Miles, Princeton, NJ (US); Mikhail Shneider, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 226 days.

(21) Appl. No.: 11/541,396

(22) Filed: Sep. 29, 2006

(65) Prior Publication Data

US 2009/0001889 A1 Jan. 1, 2009

Related U.S. Application Data

(60) Provisional application No. 60/722,025, filed on Sep. 29, 2005.

(51) Int. Cl.
*B23K 26/00* (2006.01)
*B23K 26/02* (2006.01)
*B23K 26/14* (2006.01)
*G01N 27/00* (2006.01)

(52) U.S. Cl. ............... 315/111.21; 315/149; 250/336.1; 219/121.6; 219/121.61; 219/121.83

(58) Field of Classification Search .............. 250/336.1; 315/111.21, 149; 219/121.6, 121.61, 121.83
See application file for complete search history.

(56) References Cited

U.S. PATENT DOCUMENTS 3,547,540 A   12/1970  Shigemoto
4,612,641 A   9/1986   Corkum
4,733,073 A   3/1988   Becker et al.
5,015,855 A * 5/1991   Braunlich et al. ........... 250/337
5,229,304 A   7/1993   Chang et al.
5,406,214 A   4/1995   Boda et al.
6,008,496 A   12/1999  Winefordner et al.
6,191,386 B1 * 2/2001  Albright et al. .......... 219/130.4
6,211,961 B1  4/2001   Maris
6,995,841 B2  2/2006   Scott et al.

(Continued)

FOREIGN PATENT DOCUMENTS

WO    WO 2008/092129 A2    7/2008

OTHER PUBLICATIONS

Miles, et al. "Remote Detection of Chemical and Biological Agents Through Laser Photo-Ionization Enhanced Radar Scattering," Jun. 28, 2004, (7 pages).

(Continued)

*Primary Examiner*—Nikita Wells
(74) *Attorney, Agent, or Firm*—McCarter & English, LLP

(57) ABSTRACT

A method and apparatus for remotely monitoring properties of gases and plasmas is disclosed. A laser beam is focused at a desired region within a gas or plasma to be analyzed, generating an ionized sample region in the gas or plasma. A beam of microwave radiation is directed toward the ionized sample region, and a portion of the microwave radiation is scattered by the ionized sample region and Doppler-shifted in frequency. The scattered, frequency-shifted microwave radiation is received by a microwave receiver, and is processed by a microwave detection system to determine properties of the gas or plasma, including velocities, temperatures, concentrations of molecular species, and other properties of the gas or plasma.

70 Claims, 18 Drawing Sheets

U.S. PATENT DOCUMENTS

| | | | |
|---|---|---|---|
| 7,033,781 | B1 | 4/2006 | Short |
| 2005/0167410 | A1 | 8/2005 | Bourne et al. |
| 2006/0142746 | A1 | 6/2006 | Friedman et al. |
| 2006/0219710 | A1 | 10/2006 | McManus et al. |
| 2008/0245964 | A1* | 10/2008 | Miles et al. .................. 250/288 |

OTHER PUBLICATIONS

Zhang, et al., "Diagnostics by RADAR REMPI: Microwave Scattering From Laser-Induced Small-Volume Plasmas," American Institute of Aeronautics and Astronautics, 2006 (9 pages).

Schneider, et al., "Microwave Diagnostics of Small Plasma Objects," Journal of Applied Physics, 98, 033301, 2005 (3 pages).

"Air Force Office of Scientific Research Supports New Laser Detection Concept," Air Force Reasearch Laboratory, Air Force Ofice of Scientic Research, Aug. 2006 (2 pages).

PCT International Search Report in connection with International Publication No. WO 2008/092129 A2 (3 pages).

PCT Written Opinion of the International Searching Authority in connection with International Publication No. WO 2008/092129 A2 (8 pages).

Clark, et al., "Multiphoton Processes in Open Atmosphere in the Wavelength Region 224-230 nm," J. Phys. D: Appl. Phys. 26 (1993) pp. 2107-2111 (5 pages).

Zhang, et al., "Plasma Generation in an Organic Molecular Gas by an Ultraviolet Laser Pulse," J. Appl. Phys. 73 (10), May 15, 1993, pp. 4779-4784 (6 pages).

Zhang, et al. "Microwave Diagnostics of Laser-Induced Avalanche Ionization in Air," Journal of Applied Physics 100, 074912 (2006) (6 pages).

Luo, et al., "Highly Excited States of Nitric Oxide Studied by High-Resolution Resonance-Enhanced Multiphoton Ionization Spectroscopy," Chemical Physics 153 (1991) pp. 473-481 (9 pages).

Cool, "Quantitative Measurement of NO Density by Resonance Three-Photon Ionization," Applied Optics, vol. 23, No. 10, May 15, 1984, pp. 1559-1572 (14 pages).

Tjossem, et al., "Two-Photon Resonance REMPI Detection of the Formyl Radical$^{a)}$," J. Chem. Phys. 84 (10), May 15, 1986, pp. 5334-5343 (10 pages).

Parker, et al., "Photoelectron and Photofragment Velocity Map Imaging of State-Selected Molecular Oxygen Dissociation/Ionization Dynamics," J. Chem. Phys. 107 (7), Aug. 15, 1997, pp. 2357-2362 (6 pages).

Miles, et al., "Doppler Radar REMPI," disclosure associated with AFOSR and Texas A&M University (DARPA), Aug. 30, 2005 (11 pages).

Shneider, et al., "Microwave Diagnostics of Small Plasma Objects," Journal of Applied Physics, vol. 98, 033301 (2005), published online on Aug. 4, 2005 (3 pages).

Zheltikov, et al., "Radar Return Enhanced by a Grating of Species-Selective Multiphoton Ionization as a Probe for Trace Impurities in the Atmospher," Appl. Phys. B 53, pp. 149-153 (2006), published online on Dec. 17, 2005 (5 pages).

Zhang, et al. "Microwave Diagnostics of Laser-Induced Small-Volume Plasma," 44th AIAA Aerospace Sciences Meeting and Exhibit, Reno, Nevada, Jan. 9-12, 2006 (6 pages).

Zhang, et al., "Microwave Diagnostics of Laser-Induced Avalanche Ionization in Air," Journal of Applied Physics, vol. 100, 074912 (2006), published online on Oct. 12, 2006 (6 pages).

Zhang, et al., "Diagnostics by Radar REMPI: Microwave Scattering from Laser-Induced Small-Volume Plasmas," 25th AIAA Aerodynamic Measurement Technology and Ground Testing Conference, San Francisco, California, Jun. 5-8, 2006 (9 pages).

* cited by examiner

METHOD AND APPARATUS FOR REMOTELY MONITORING PROPERTIES OF GASES AND PLASMAS

RELATED APPLICATIONS

The present application claims the benefit of U.S. Provisional Application Ser. No. 60/722,025 filed Sep. 29, 2005, the entire disclosure of which is expressly incorporated herein by reference.

STATEMENT OF GOVERNMENT INTERESTS

The present invention was made with Government support. Accordingly, Government has certain rights to the present invention.

BACKGROUND OF THE INVENTION

1. Field of the Invention

The present invention relates to the determination of properties of objects. More specifically, the present invention relates to a method and apparatus for remotely monitoring properties of gases and plasmas.

2. Related Art

In aerospace engineering and other disciplines, it is often important to remotely monitor and determine properties of objects, such as gases and plasmas. For example, it is often desirable to remotely identify species of gases and plasmas, as well as to measure selected state populations, velocities, rotational and vibrational temperatures, thermodynamic properties, and nonequilibrium conditions which may exist in such gases and plasmas. Further, the ability to remotely determine properties of gases and plasmas is especially useful in studying hypersonic flows immediately behind a shock, in a wake, or in a boundary layer region where complex velocity fields exist and where nonequilibrium states and chemical reactions may be occurring.

Resonant, Enhanced, MultiPhoton Ionization (REMPI) is a known, ultra-high sensitivity probing technique for detecting low concentrations of molecular species in gases. In REMPI, a single, tunable laser is used to ionize a region within a gas, and properties of the ionized region are analyzed. REMPI is an effective spectroscopic tool because the multiphoton ionization cross-section is strongly enhanced by resonant intermediate states. This enhancement can be due to single photon or multiphoton resonances. As a laser is tuned through these resonances, the ionization yield reflects the spectrum of the resonances, thereby providing an indication of molecular species in a gas.

FIG. 1 is a diagram illustrating the REMPI technique. The (n+m) REMPI process can be characterized by the absorption of n photons to a resonant state followed by the absorption of m additional photons to ionization, Thus, a first type of REMPI excitation process, which is referred to as a (1+1) process, is characterized by a single photon resonance (i.e., a single photon exciting from the ground state of an atom or molecule to one or more intermediate states) followed by a single photon exciting the atom or molecule from that intermediate state to above an ionization threshold. A second type of REMPI excitation process, which is referred to as a (2+1) process, is characterized by a two photon resonance (i.e., two photons exciting from a ground state to one or more intermediate states) and a single photon exciting to above an ionization threshold. Additional REMPI processes, including 3+1, 4+1, etc. are possible. A third type of REMPI excitation process, which is referred to as a (2+2) process, is characterized by a two photon resonance followed by two photons exciting to above an ionization threshold. Additional REMPI processes with multiple photons required for ionization are also possible. In each of these cases, the photon resonance energy and the energy required for ionization can be analyzed to determine properties of the gas or plasma under study. The selection of which of these (n+m) REMPI excitation processes to use depends on the particular molecule and the available source laser. Usually, the intermediate state is in the ultraviolet portion of the electromagnetic spectrum, so the 1+1 process requires a tunable ultraviolet laser, but higher order processes such as the 2+1 and 2+2 processes may be achieved using a visible or near-ultraviolet source.

In conventional REMPI applications, low pressure gases are used and ionization is measured using electrodes or wire probes. A direct current (DC) potential sweeps charges out of the ionized region, which generates a pulse of current through a detector system when the REMPI-generated ionization occurs. REMPI has also been applied at higher pressures using small probe detectors and in flames using the conductivity of the flame, which is in contact with two electrodes. However, conventional REMPI applications are limited because of the need to sweep the charges out of the ionized region to facilitate detection. Further, electrodes or wire probes must be in physical contact with the ionized region, thereby preventing remote measurement and detection of properties of gases and plasmas.

A number of techniques have been developed for the measurement of velocities of gas flows. Velocity is a fundamental transport parameter in a gas flow, and its measurement is of primary importance both for characterizing the flow and for validating predictive models of the flow. Often, it is the velocity in a specific location that is of most importance, such as the velocity close to a surface, behind a shock, or in the wake of an airfoil. Laser Doppler Velocimetry (LDV) and Particle Imaging Velocimetry (PIV) are known techniques for measuring flow velocities. However, both limited by a random arrival of particles at a location of interest. In addition, these methods suffer from particle "slip" in high speed flows and near surfaces, where the particle density may be particularly low.

Flow tagging approaches have also been developed, based on vibrational excitation of oxygen, creation of NO, and other approaches. However, these approaches are not effective in high temperature environments where vibrationally-excited molecules are already present and/or radical chemical species may already be present. Velocity measurement by laser breakdown has been used, but it introduces large perturbations into the flow, and tracking of the breakdown by shadowgraph or schlieren limits this approach to flows with low complexity and simple geometries.

Temperature measurements in a high-speed flow and in combusting environments are always difficult to perform. For instance, intrusive probes perturb the flow or the combustion process. As a result, various non-perturbative approaches have been developed, including Laser Induced Fluorescence (LIF), Rayleigh scattering, and Coherent Anti Stokes Raman Scattering (CARS). However, each of these approaches has limitations. The LIF methods are subject to quenching errors and cannot easily be applied in air flows since there is no convenient fluorescing species. Rayleigh scattering is subject to interference from background light and relies on knowledge of the species mole fractions. In its most common implementation, a Rayleigh measurement is of a density and so pressure must be known and the ideal gas law used to convert to temperature. CARS measurements are quite complex, and proper fitting of spectral information becomes very difficult for complex gas mixtures.

Accordingly, what would be desirable, but has not yet been provided, is a method and apparatus for remotely monitoring properties of gases and plasmas which addresses the foregoing limitations of existing monitoring techniques.

SUMMARY OF THE INVENTION

The present invention relates to a method and apparatus for remotely monitoring properties of gases and plasmas. A pulsed laser beam is focused at a desired region within a gas or plasma to be analyzed, generating an ionized sample region. A beam of electromagnetic radiation, such as microwave radiation, is directed toward the ionized sample region. A portion of the electromagnetic radiation is scattered by the ionized sample region, and, depending on the velocity of the region relative to the source of electromagnetic radiation, may be Doppler-shifted in frequency. The time dependence of the scattered electromagnetic radiation amplitude depends on the local thermodynamic environment including the temperature, density, and species of the gas or plasma. In the case of a strong spark generated in the gas or plasma, the amplitude time dependence also reflects the changing physical properties of the ionization region.

The scattered, time-dependent, and frequency-shifted electromagnetic radiation is received by a receiver (e.g., a microwave scattering detector) and processed by a detection system, such as a heterodyne or homodyne microwave detection system, to determine properties of the gas or plasma, including velocities, temperatures, concentrations of molecular species, and other properties of the gas or plasma. A second receiver could be used to provide two-dimensional indications of velocity, and a third receiver could be used to provide three-dimensional indications of velocity. Separately located receivers can also be used to monitor the physical dimensions and refractive index changes of the laser-generated ionization region by establishing time-evolving scattering patterns from the relative signal strengths. Multiple electromagnetic transmitters and receivers operating at different frequencies may also be used to monitor the same laser-generated ionization region to provide further information regarding the properties of the gas or plasma. A frequency-tunable laser beam can be used to allow for precise, remote measurements of species, temperatures, and non-equilibrium states of gases and plasmas through signatures associated with the energies of the intermediate states.

BRIEF DESCRIPTION OF THE DRAWINGS

For a better understanding of the present invention, references is made to the following Detailed Description of the Invention, taken in connection with the accompanying drawings, in which.

DETAILED DESCRIPTION OF THE INVENTION

Figure 1:
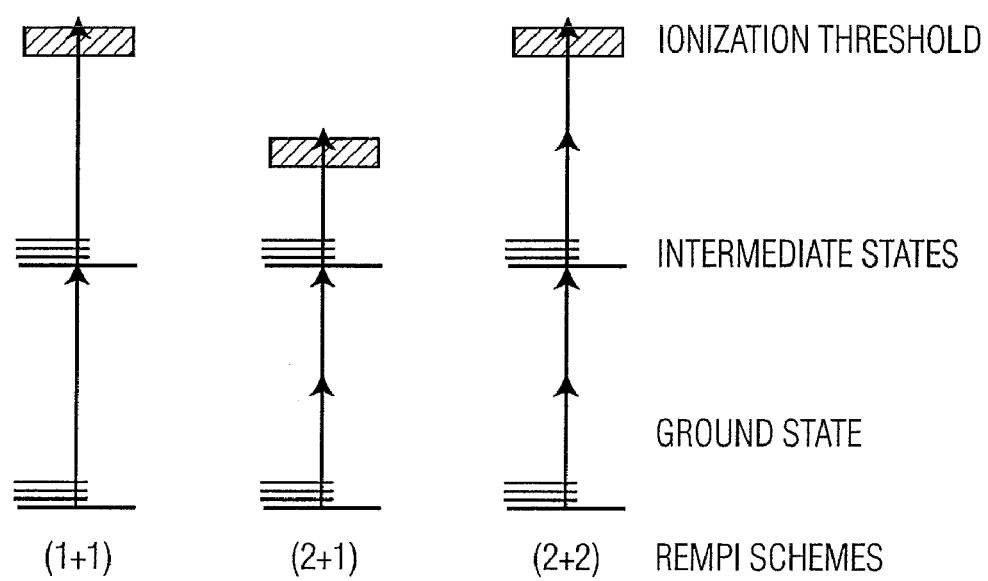
FIG. 1 is a diagram showing various REMPI schemes achieved in the prior art.

The present invention relates to a method and apparatus for remotely monitoring properties of gases and plasmas. The present invention is operable with conventional REMPI techniques, such as those shown in FIG. 1.

Figure 2:
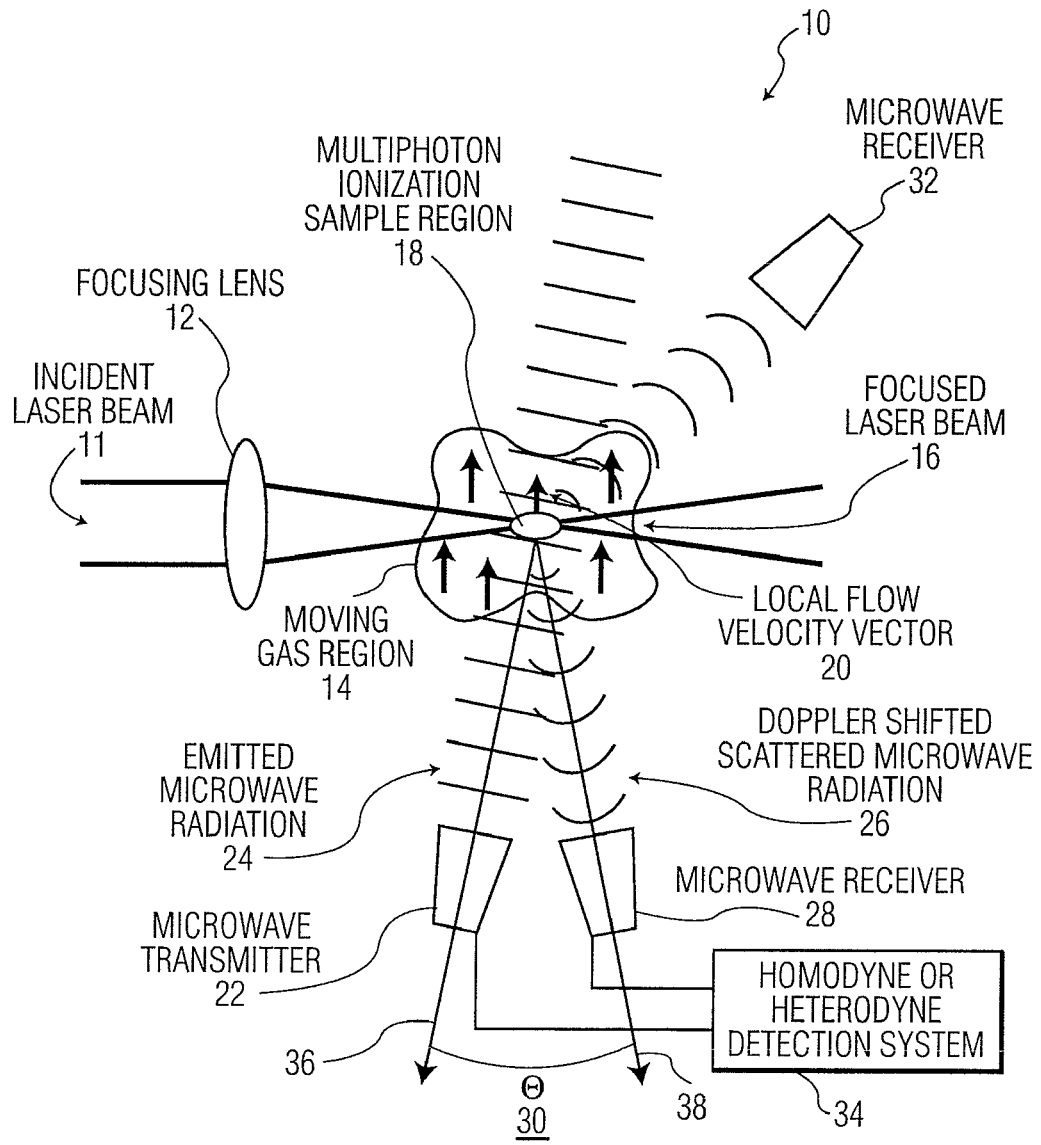
FIG. 2 is a diagram of an apparatus constructed in accordance with the present invention, which allows for remote measurement of velocities and temperatures of gases and plasmas.

FIG. 2 is a diagram showing an apparatus constructed in accordance with the present invention for remotely monitoring properties of gases and plasmas. The apparatus, indicated generally at 10, includes a pulsed incident laser beam 11 and a lens 12 for producing a focused laser beam 16. The laser beam 16 is focused into a gas or plasma region 14 to create a multiphoton, ionization sample region 18. The ionized sample region 18 could be created using known REMPI techniques, or any other, suitable ionization technique. A short laser pulse produces high power, but has little energy (e.g., a few millijoules). When the laser beam 11 is tuned to a multiphoton transition of a species, such as oxygen, the laser beam 11 has the capability of producing a small plasma volume without a large deposition of energy. This is in contrast to typical laser breakdown, in which tens to hundreds of millijoules of energy are deposited into a flow, resulting in shock waves being generated and a significant entropy (hot) spot being created. The laser beam 11 could be generated using a nanosecond Nd:YAG laser, or any other suitable laser. The region of ionization 18 moves in the direction of the local flow velocity vector 20. The apparatus 10 also includes a microwave transmitter 22 and a microwave receiver 28 oriented with respect to each other at an angle Θ (indicated by reference numeral 30). A homodyne or heterodyne detection system 34 is coupled to the microwave transmitter 22 and the microwave receiver 28.

The microwave transmitter 22 emits a beam 24 of microwave radiation that passes through the region of ionization 18. The ionized gas in the region of ionization 18 scatters the microwave radiation, such that the frequency of the radiation is shifted by the Doppler effect depending upon the velocity of the region of ionization 18 relative to the microwave transmitter 22 and receiver 28. The time dependence of the microwave signal amplitude depends on the local thermodynamic environment, including temperature, density, and species of the gas or plasma. If the region of ionization 18 is created through spark generation, the time dependence also reflects the changing physical properties of the region of ionization 18. Microwave scattering arises from an induced dipole associated with a small coherent plasma volume. The scattered, frequency-shifted microwave radiation (indicated by reference numeral 26) is then received by the microwave receiver 28. The frequency shift is a function of the projection of the moving gas velocity vector 20 onto the bisector of the angle Θ formed by the line 36 extending between the microwave transmitter 22 and the ionized region 18, and the line 38 extending between the microwave receiver 28 and the ionized region 18.

Optionally, a second microwave receiver 32 can be provided at a different angle (i.e., at an angle to the microwave transmitter 22 other than the angle Θ) so that a second projection of the velocity vector 20 can be measured. A third, out-of-plane, microwave receiver (not shown) could also be provided, so as to generate a third projection of the velocity vector 20. Using three receivers, a full, three-dimensional velocity vector can be remotely determined. The second microwave receiver 32 and the third microwave receiver can each be connected to the homodyne or heterodyne detection system 34. It should be noted that separately located receivers can also be used to monitor the physical dimensions and refractive index changes of the region of ionization 18 by establishing time-evolving scattering patterns from the relative signal strengths. Further, multiple microwave transmitters and receivers operating at different frequencies may also be used to monitor the region of ionization 18 to provide further information regarding the properties of the gas or plasma. Additionally, microwave detector arrays can be provided, or a single detector can be moved about the gas or plasma, to observe multiple pulses and to determine the microwave scattering pattern. In such a manner, the size and refractive index of the ionization volume element can also be detected.

The frequency shift of the radiation generated by the microwave transmitter 22 and measured by the microwave receiver 28 (and, optionally, the microwave receiver 32 and a third microwave receiver, if used) is determined by the homodyne or heterodyne detection system 34. The system 34 compares the frequency and/or phase of the detected microwave radiation with either the frequency and/or phase of the transmitted microwave radiation (i.e, homodyne detection) or the frequency and/or phase of a reference microwave source (i.e., heterodyne detection) to determine the frequency shift. Such shift provides an indication of the velocity of the moving gas region 14. The velocity of the ionized region 18 also reflects the thermal motion of the gas, thus providing an indication of temperature of the moving gas or plasma region 14. In such circumstances, the frequency-shifted, scattered microwaves 26 contain a range of frequencies that reflect the distribution of velocities associated with a particular temperature. The detected frequency shift of the scattered microwaves can be used to measure temperature of a gas by recording a distribution of frequency shifts that arise from the thermal motion of the gas. An advantage of this approach is that the temperature and velocity measurements are accomplished in a single laser pulse. The temperature causes the scattering plasma volume to consist of subsets of various velocity groups that each produce a Doppler shifted scattering. Thus, thermal motion leads to a broadening of the microwave scattered signal.

The motion detected by the present invention is that of the coherent kernel, since the scattering results from the induced dipole. The microwave scattered signal is broadened by the motion of the electrons. After a short equilibration time, the temperature of the electrons falls to the ambient gas temperature which reflects the temperature of the neutrals. The fact that the electrons are thousands of times lighter than the neutral species causes the thermal frequency broadening of the scattered electromagnetic radiation to be significantly wider and thus more easily detected than if it were only scattered from the neutral species. The REMPI ionization process transfers very little momentum to the gas, so the thermal motion is not strongly affected as long as the transferred energy is small and an "explosion" is avoided. If a flow is moving, the ionized region moves with it, and scattered electromagnetic radiation is frequency shifted by the Doppler effect. The frequency shift can be measured with the detector 34. For example, a heterodyne detector that generates a beat frequency with a reference source can be used. Alternatively, a homodyne detector that generates a beat frequency with a transmitting source can be used. The measured frequency shift can be converted to a specific velocity component, since the location of the microwave source, the scatterer, and the detector are known.

The laser-generated ionization region 18 will continue to scatter the microwaves until the electrons are lost due to attachment or recombination. The rate at which the attachment or recombination occurs provides another measurement of the local properties of the gas or plasma. This rate can be shown to be strongly dependent on the local temperature and density and on the particular species that are present. If multiple electromagnetic sources and detectors are used to observe the ionization region at different wavelengths, then, due to the frequency dependence of the scattering process, different properties of the local environment can be preferentially highlighted.

The focused, pulsed laser beams implemented by the present invention produce a small-volume, non-stationary plasma that is on the scale of tens of microns in diameter and less than a few millimeters in length. The incident electromagnetic radiation modulates the charge separation in that plasma, creating an oscillating induced dipole. The wavelength of the incident electromagnetic radiation is, in general, much larger than the size of that plasma. If the skin layer, $\delta = 2/\sqrt{2\mu_0 \sigma \omega_m}$ at the electromagnetic frequency $\omega_m$ and with plasma conductivity $\sigma$, is greater than the characteristic size of the plasma, all the electrons in the plasma oscillate in the same phase. As a result, in the far field, the plasma can be regarded as an induced point dipole radiation source of electromagnetic waves, and the scattering falls into the Rayleigh scattering approximation. In that case, the scattered electromagnetic signal level is directly proportional to the square of the number of electrons. The scattering pattern of the electromagnetic waves is a classical dipole pattern shape with no amplitude variation about the induced polarization axis and a sinusoidal variation in the azimuthal angle. On the other hand, if the skin layer is small, then some of the electrons are shielded. In that case, the scattering falls into the Mie regime and no longer has a dipole character, and the electromagnetic scattering amplitude will vary around the polarization axis in a manner that is associated with the size, shape, refractive index and conductivity of the ionized volume element. The Rayleigh range is particularly interesting since in that regime, the electromagnetic scattering intensity provides a quantitative method for measuring the ionization, evolution, and electron loss process.

In the far field, where the distance between the receiver and the plasma is much greater than the electromagnetic wavelength λ, which, in turn, is much greater than the scale of the plasma, L, the total intensity of coherently scattered electromagnetic radiation averaged over a cycle can be found from the following expression:

$$\langle \Theta \rangle = \frac{I_{m0} V^2 \omega_p^4 \omega_m^4}{6\pi c^4 [(\omega_p^2 - \omega_m^2)^2 + (v_{en}\omega_m)^2]} = \frac{I_{m0} \omega_m^4}{6\pi c^4 [(\omega_p^2 - \omega_m^2)^2 + (v_{en}\omega_m)^2]} \frac{e^4 N^2}{\varepsilon_0^2 m_e^2} \quad \text{Equation 1}$$

where $\omega_p$ is the plasma radial frequency which is proportional to the square root of the free-electron number density, $\omega_m$ is the electromagnetic radial frequency, $v_{en}$ is the electron-neutral collision frequency, $I_{m0}$ is the incident electromagnetic radiation intensity, V is the volume of the ionization region, N is the number of free electrons in the laser generated plasma, and c, e, $\varepsilon_0$ and $m_e$ are constants corresponding to the speed of light, the electron charge, the free space permittivity and the rest mass of an electron. Note that the frequency of the electromagnetic radiation will change the scattering amplitude and also the sensitivity of the measurement of the electron neutral collision frequency, so observing the ionization region with multiple electromagnetic frequencies provides more information about the local gas or plasma properties. In the collision dominated regime where $v_{en} \gg \omega_m, \omega_p$, the effective total "Rayleigh" scattering cross section $\sigma_R$, can be written as:

$$\sigma_R = \frac{\langle \Theta \rangle}{I_{m0}} = \frac{e^4 \omega_m^2}{6\pi \varepsilon_0^2 m_e^2 v_{en}^2} N^2 \quad \text{Equation 2}$$

The effective differential cross section is:

$$\frac{\partial \sigma_R}{\partial \Omega} = \frac{3}{8\pi} \sigma_R \sin^2 \phi \quad \text{Equation 3}$$

where φ is the angle between the polarization of the induced dipole and the direction of scattered signal. θ is the angle in the plane normal to the polarization vector and θ=0 is defined to be along the y axis, orthogonal to the propagation direction of the incident electromagnetic wave. Note that for the experiments discussed herein below, the laser propagates in the direction of the electromagnetic (microwave) polarization vector. This selection helps to assure that the induced polarization vector lies in the same direction as the polarization of the incident electromagnetic radiation.

There are two principal mechanisms for the generation of ions: multiphoton ionization and avalanche breakdown. The avalanche breakdown requires that a low concentration of electrons be present in the gas and is the typical mechanism for high energy laser breakdown. It leads to high heating and a large electromagnetic scattering signal if the ionization region is illuminated with electromagnetic waves during and after the breakdown event. Multiphoton ionization requires very high intensity unless there are intermediate resonant states, as in the REMPI process. In that case, ionization can be achieved at much lower energies and is much less perturbative. In some cases with high energy REMPI pulses, the REMPI process provides the initial electrons for a following avalanche process.

According to the simplified theory of avalanche optical breakdown, the ionization rate under the applied laser field $E_L = \text{Re}[E_0 \exp(-i\omega_L t)]$ can be expressed as:

$$v_i = \frac{e^2 E_0^2 v_{en}}{2 m_e (\omega_L^2 + v_{en}^2)} \frac{1}{\xi_{ion}} = \frac{e^2 I_L v_{en}}{m_e (\omega_L^2 + v_{en}^2) \varepsilon_0 c} \frac{1}{\xi_{ion}} \quad \text{Equation 4}$$

where $E_0$ is the laser field strength, $\omega_L$ is the laser radial frequency, $\xi_{ion}$ is the ionization threshold in joules (usually given in electron volts, which then must be multiplied by e, the electron charge, to get joules), and $I_L$ is the intensity of the laser. It is assumed that the ionization during the avalanche phase is mainly due to the collisions between electrons and neutrals and that there is no energy loss for electrons other than ionization. These assumptions are valid for the initial stages of laser-induced breakdown, when the ionization rate is much greater than the losses due to recombination and diffusion. However, these assumptions do not apply at the late stage of breakdown where electron-electron collisions and Coulomb interaction dominate.

For room air (N2:O2=4:1) the ionization threshold can be approximated as follows:

$$\xi_{ion} \approx \xi_{ion,O_2} \xi_{ion,N_2}/(0.8\xi_{ion,O_2} + 0.2\xi_{ion,N_2}) \approx 14.77 \text{ eV} \quad \text{Equation 5}$$

where $\xi_{ion,N_2}$ and $\xi_{ion,O_2}$ are ionization threshold of $N_2$ and $O_2$, respectively.

At the initial stage of the breakdown, the plasma volume is approximately the same as the laser focus size. Electrons mainly collide with neutrals, and the electron number density, $n_e$, approximately follows the following relationship:

$$\frac{dn_e}{dt} = v_i n_e \quad \text{Equation 6}$$

The electron number density can be expressed as:

$$n_e = n_{e0} \exp\left(\int_0^t v_i \, dt'\right) \quad \text{Equation 7}$$

The expression for the microwave scattering signal intensity in terms of the parameters of the laser and the electromagnetic source during the precursor rise can be derived by combining Equations 2 and 6. The scattered electromagnetic signal intensity becomes:

$$\langle \Theta \rangle \propto I_{m0} \omega_m^2 V^2 n_{e0}^2 \exp\left(2 \int_0^t v_i \, dt'\right) \propto I_{m0} \omega_m^2 V^2 \sigma_\omega^2 \quad \text{Equation 8}$$

where $$\sigma_\omega(t) = \frac{e^2 n_e(t) v_{en}}{m(v_{en}^2 + \omega_m^2)}$$

is the high-frequency conductivity of the weakly ionized plasma during the initial avalanche phase of a laser breakdown. During the breakdown phase, electrons have temperature $T_e \sim 1$ eV which is estimated from the experimental value of the electron mobility and the collision frequency is $v_{en} \approx 3.5 \times 10^9 \cdot p \cdot 300/T$, where p and T are the gas pressure in Torr and the gas temperature in Kelvin. Following breakdown, the electrons rapidly cool to the local gas temperature.

During the typical precursor rise time, when only avalanche ionization is included, the plasma volume $V_0$, the incident microwave intensity, the electromagnetic frequency, and the initial number density of electrons can be considered constant. Taking into account the condition of plasma transparency, $\delta > V_0^{1/3}$, from Equation 8 it follows that the scattered signal intensity is:

$$I_s \propto <\Theta> \propto \exp\left(2\int_0^t v_i \, dt'\right) \quad \text{Equation 9}$$

where $v_i$ ($I_L$,t') is the ionization rate, which is a function of laser intensity $I_L$ as in Equation 4, i.e. $v_i \propto I_L$. This indicates that the observed signal associated with the electromagnetic wave scattering from the laser induced ionization region increases in an exponential fashion until saturation is reached. The time delay associated with the rise of the electromagnetic scattering is related to the laser intensity and to the initial number of electrons in the laser focal volume.

Figure 3:
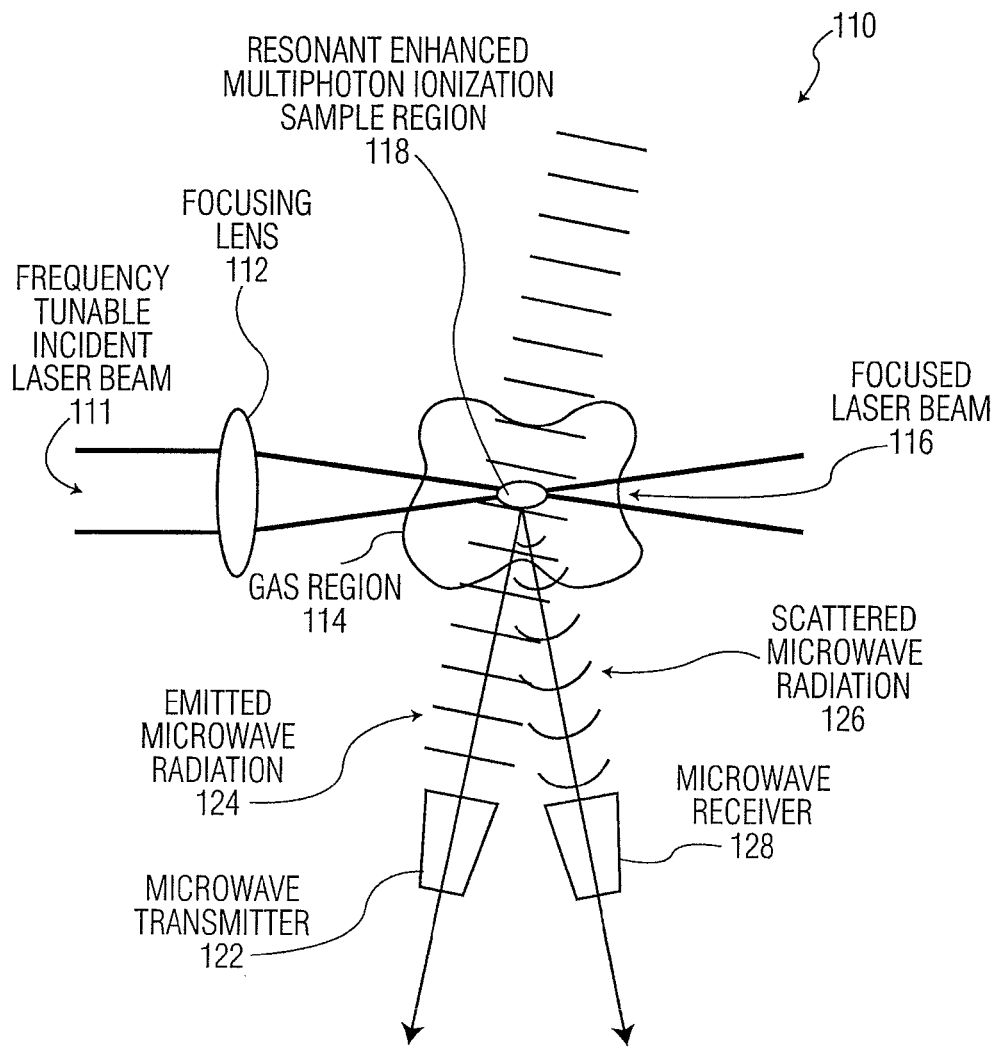
FIG. 3 is a diagram of an apparatus constructed in accordance with another embodiment of the present invention, which allows for remote measurement of species, temperature, and nonequilibrium states of gases and plasmas.

FIG. 3 is a diagram showing another embodiment of the apparatus of the present invention, indicated generally at 110. In this embodiment, the apparatus 110 can measure species, temperatures, and non-equilibrium population states. The apparatus 110 includes a frequency-tunable, incident laser beam 111 and a lens 112 for producing a focused laser beam 116. The focused laser beam 116 produces an ionized sample region 118 in a gas or plasma region 114, using known REMPI techniques. The frequency of the laser beam 111 is tuned, so that the ionization level changes in the sample region 118 in a manner which reflects the molecular energy levels of the particular species of gas in the sample region 118. A microwave transmitter 122 transmits a beam 124 of microwave radiation through the sample region 118. A portion of the radiation is scattered by the ionized plasma in the sample region 118 and reflected in a beam of microwave radiation 126. The reflected radiation is received by a microwave receiver 128. The microwave transmitter 122 and the microwave receiver 128 can be connected to a homodyne or heterodyne detection system, such as the system 34 of FIG. 2.

By recording the strength of the microwave radiation received by the microwave receiver 128 as a function of the frequency of the laser beam 111, the population of the various molecular energy states of specific molecules in the sample region 118 can be determined. The presence of specific spectral features indicates the presence of corresponding molecules within the region 118. The strength of the scattered microwave radiation indicates the level of ionization, and thus, the population of the particular energy levels associated with a particular species. By comparing the strength of scattered radiation from one energy level to scattering from another energy level, the relative population of the gas or plasma region 114 can be determined. From this information, if the molecules are in thermal equilibrium, the temperature of the gas or plasma 114 can also be determined. If the molecules are not in thermal equilibrium, then a separate rotational and vibrational temperature can be determined if these modes have separately reached thermal equilibrium. Otherwise, the relative populations of the energy levels provide a measurement of the non-equilibrium state of the molecule under examination.

Figure 4:
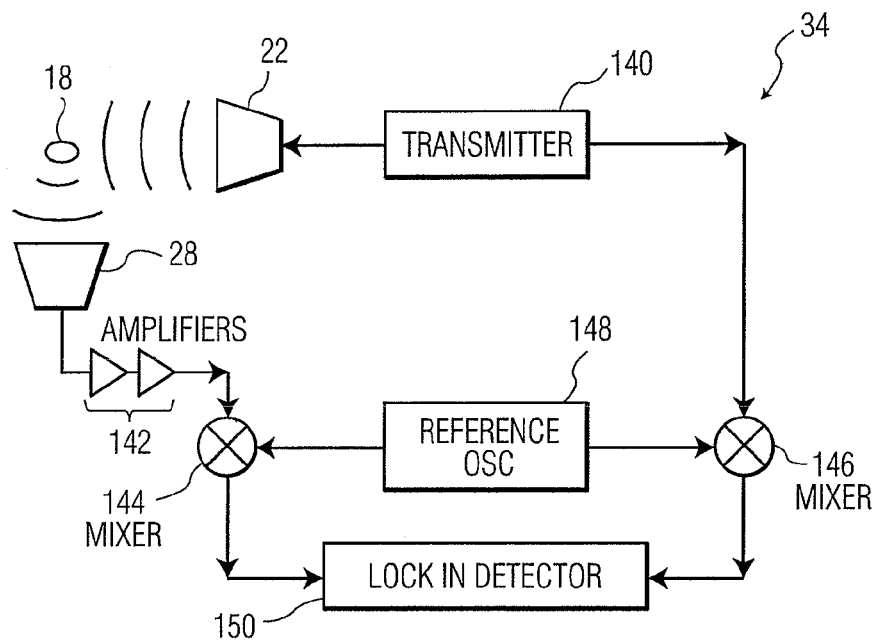
FIG. 4 is a diagram of a heterodyne microwave detection system employed by the present invention.

FIG. 4 is a diagram showing the microwave detection system 34 of FIG. 2 in greater detail. As mentioned above, the present invention could be operated with a homodyne or a heterodyne detection system. The system 34 shown in FIG. 4 is a heterodyne detection system. The system 34 is connected to the microwave transmitter 22 and the microwave receiver 28 of FIG. 4. Optionally, the system 34 could be connected to the second microwave receiver 32 of FIG. 2, as well as a third microwave receiver. The system 34 includes a frequency offset reference oscillator 148 and a lock-in detector 150. A microwave transmitter 140 generates microwaves which are sent to the transmitter 22 for transmission to the sample region 18.

The microwaves scattered by the sample region 18 are collected by the microwave receiver 28 and are amplified by a broadband amplifier 142. The amplified signal is then passed into a mixer 144, where the amplified signal is mixed with a reference frequency generated by the reference oscillator 148, thereby producing a downshifted signal. A reference mixer 146 beats a signal from the microwave transmitter 140 with the reference frequency generated by the reference oscillator 148, and provides a reference beat frequency to the lock-in detector 150. The reference beat frequency is then used to the drive the lock-in detector 150, which selectively detects the frequency and phase of the downshifted signal. The heterodyne microwave detection system has exceptionally high noise rejection characteristics. The detection system 34 could also be configured as a homodyne receiver that calculates frequency and/or phase of the scattered microwave radiation by comparing same to the frequency and phase of the transmitted microwave radiation.

Figure 5:
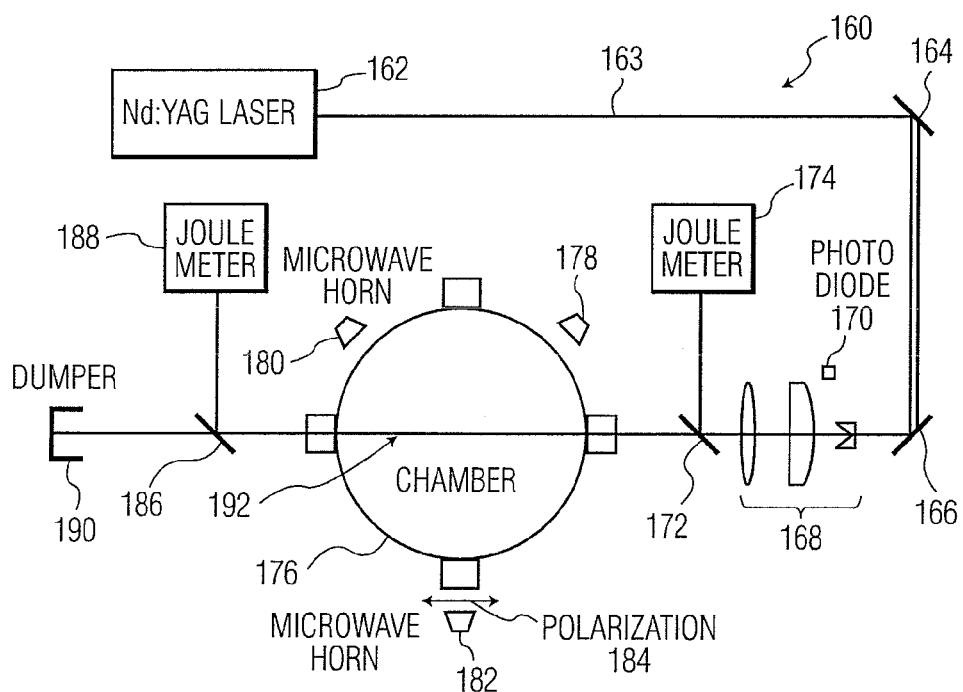
FIG. 5 is a diagram showing an experimental setup for testing the microwave detection technique of the present invention.

FIG. 5 is a diagram showing an experimental setup for testing the microwave detection technique of the present invention. A nanosecond Nd:YAG laser 162 was focused into air, and operated at a wavelength of 1.064 nm to generate an optical breakdown. The laser 162 was not tuned, so REMPI spectroscopy was not performed, but rather, microwave scattering from the avalanche breakdown region was observed to determine the feasibility of using microwave scattering to monitor avalanche ionization.

The laser 162 produced a beam 163 that was directed by reflectors 164 and 166 into a chamber 176, after being focused by optics 168. A dumper 190 collected and strongly attenuated the beam 163 after it exited the chamber 180 so that no reflective scattering from the beam was observed. A microwave horn 182, a polarizer 184, and an associated microwave transmitter (not shown) injected microwaves into the chamber 180. A portion of the microwaves were scattered by ionization region 192 at the center of the chamber 180, and the scattered microwaves were detected by microwave horns 178 and 180. Joule meters 174 and 188, and their associated dichroic mirrors 172 and 178, allowed for measurement of the laser energy entering and exiting the chamber 176, respectively.

Figure 6:
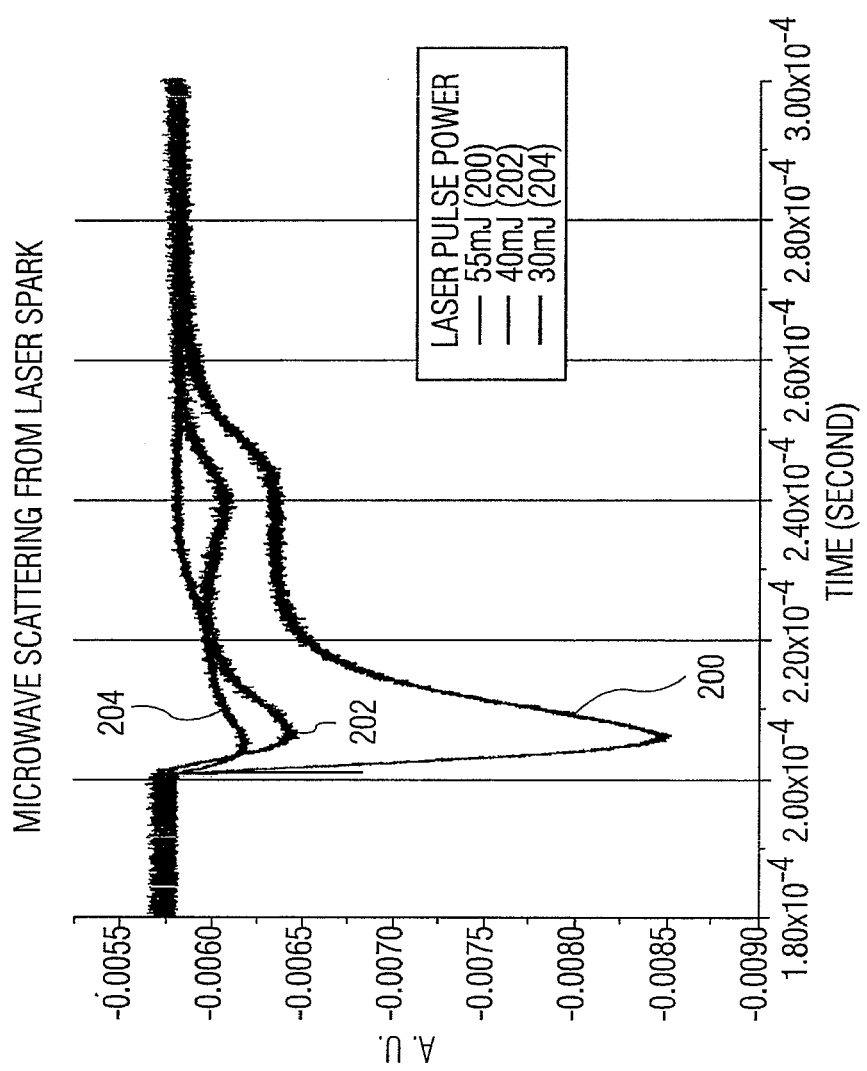
FIG. 6 is a graph showing microwave scattering detected by the present invention from a laser spark.

For the experiment depicted in FIG. 5, the microwave frequency was 12.6 GHz, corresponding to a wavelength of 2.38 cm. This wavelength is long compared to the dimensions of the laser breakdown plasma, which is approximately 3 mm in length and about 20 microns in diameter, and falls into the Rayleigh scattering range. The microwave intensity from the source microwave horn transmitter 182 was 8.8 W/m². The results of the experiment are shown in FIG. 6, which presents a graph of microwave scattering from a laser spark over time. The first trace 200 represents microwave scattering by a laser pulse of 55 mJ. The second trace 202 represents microwave scattering by a laser pulse of 40 mJ. The third trace 204 represents microwave scattering by a laser pulse of 30 mJ. Scattering amounts were measured in arbitrary units (A.U.) ranging from −0.0090 to 0.0055. As can be seen, different energy levels of the laser pulse produce different microwave scattering patterns. In particular, the rise time of the scattering decreased with increasing laser energy as predicted by Equation 9.

Figure 7:
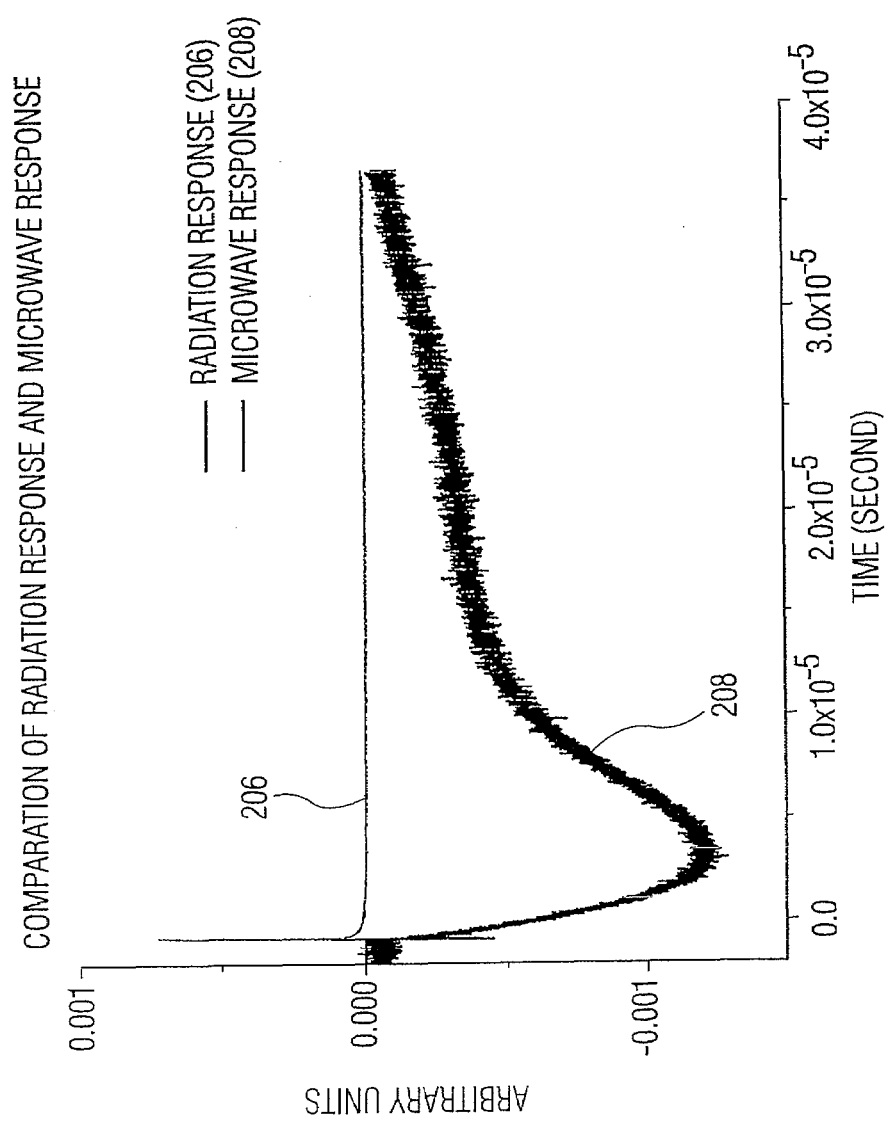
FIG. 7 is a graph showing a comparison of microwave response versus radiation response.

FIG. 7 is a graph showing the detected energy from microwave scattering produced by the experiment shown in FIG. 4. The trace 206 shows radiation power of the plasma generated by the laser, and the trace 208 shows microwave scattering. Note that the relatively long recombination time of the electrons leads to microwave scattering that persists on the order of 100-200 microseconds following breakdown of the plasma. This microwave scattering is generated by secondary electrons that are produced once the laser energy has been deposited. This signal is characteristic of strong laser induced avalanche breakdown where the ionization region evolves significantly after the laser excitation due to thermal expansion.

Figure 8:
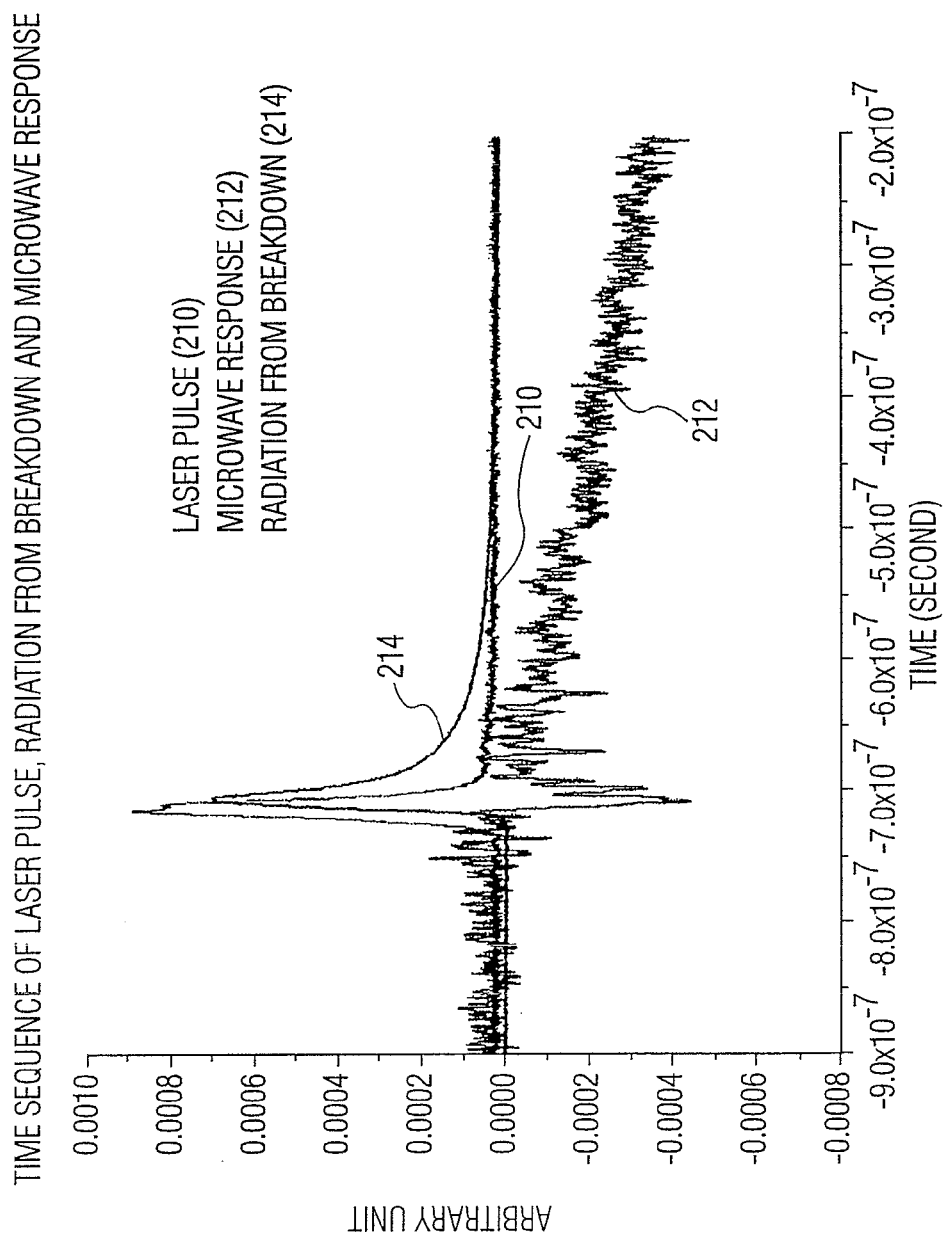
FIG. 8 is graph showing a time sequence of a laser pulse, radiation from breakdown of the laser pulse, and microwave response detected by the present invention.

FIG. 8 is a graph showing the initial portion of the time response of microwave scattering from a pulsed, laser-generated ionization region. The graph shows the laser pulse shape and time history, the time signal from the optical radiation associated with the breakdown of the plasma (the visible spark), and the microwave scattering generated by the experiment shown in FIG. 4. The laser pulse shape is seen in the initial spike of the trace 210. The microwave and radiation responses are shown in traces 212 and 214, respectively. It can be seen that the microwave signal echoes the radiation from the breakdown, indicating that the microwave scattering follows the laser-induced charge build-up. Unlike optical fluorescence, the microwave scattering follows the generation of secondary electrons and the electron recombination and attachment processes. The data depicted in FIG. 8 was generated by observing the amplified, 12.6 GHz microwave scattering without mixing and lock-in detection so that the high frequency response could be preserved. Signal-to-noise ratios on the order of 1000 times higher are expected using the heterodyne and homodyne mixing processes.

Figure 9:
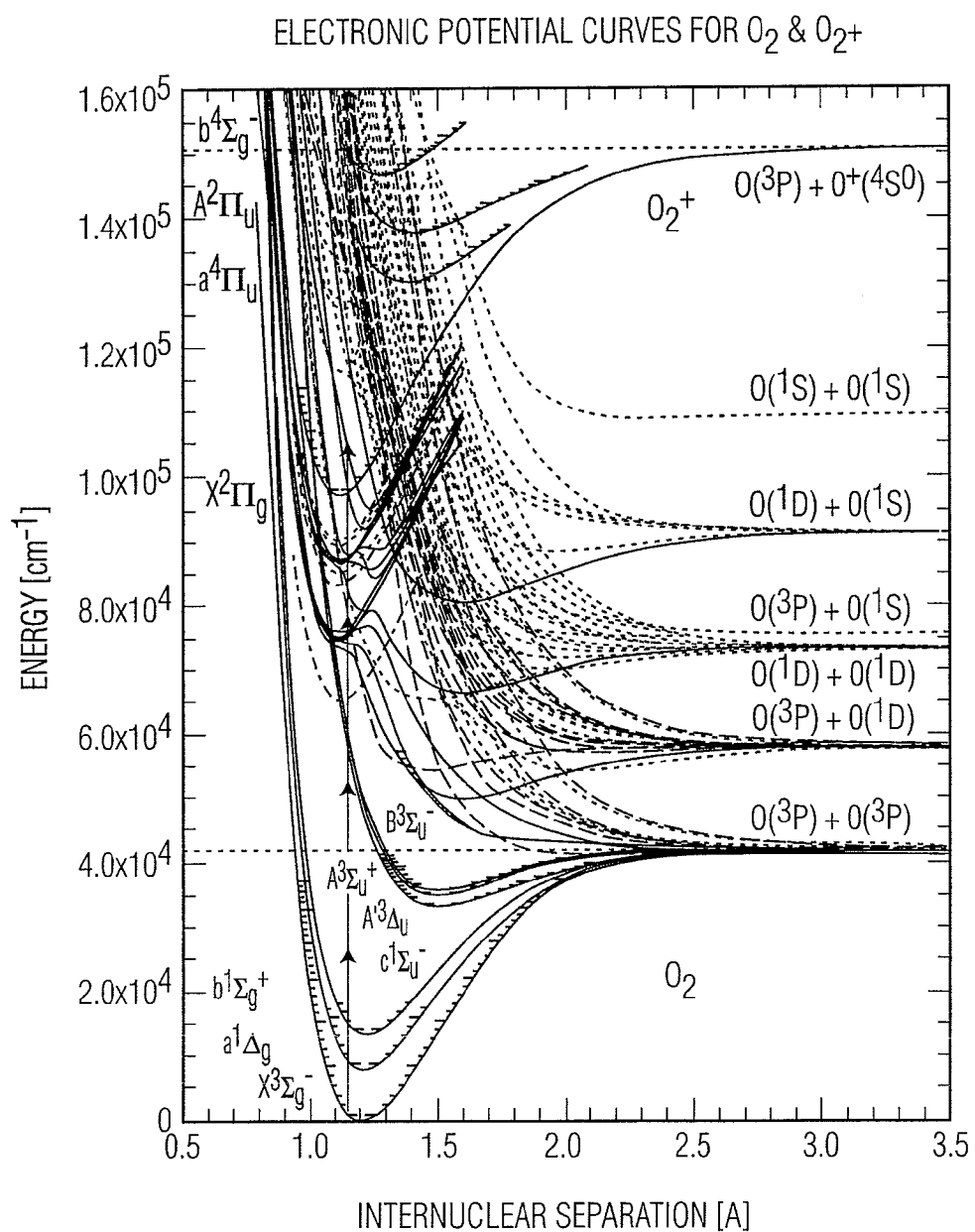
FIG. 9 is a graph showing various electronic potential curves (energy versus internuclear separation) for $O_2$ and $O_2^+$.

FIG. 9 is a graph showing various electronic potential curves (energy versus internuclear separation) for $O_2$ and $O_2^+$. The present invention can be implemented using the oxygen in air, because it represents a major species and is relatively easy to probe using either two-photon or single-photon resonant REMPI approaches. One approach is a two-photon resonant, four-photon ionization (2+2) of oxygen as shown by the arrows in FIG. 9. The present invention can be implemented to remotely measure and record the oxygen molecular spectrum by tuning the laser in the vicinity of selected spectral lines. The features of the oxygen REMPI spectrum can be used to determine the temperature, the frequency shift of the scattered electromagnetic radiation from the oxygen ionization region can be used to determine the velocity, and the electron loss rate following ionization due to electron attachment to oxygen can be used to determine density and temperature. The velocity of air flows, as well as temperatures and minor species, can also be detected in a similar manner.

The present invention can be implemented to remotely monitor a wide variety of properties of gases and plasmas. Examples include the remote monitoring of species, temperature and transport properties for plasma aerodynamic, magneto-hydrodynamic processes, high speed and complex airflows, combusting gases, and the remote measurement of atmospheric contaminants and hazardous gases. Further, the present invention can be used as a diagnostic tool for studying conditions in a hypersonic flow immediately behind a shock, in a wake, or in a boundary layer region where complex velocity fields are expected, and where nonequilibrium states and chemical reactions may be occurring. The laser can be focused to a spot on the order of tens of microns in diameter and hundreds microns long, so that precise measurements at specified locations can be made. The laser also can be conditionally fired to sample time-varying flow phenomena or precision-timed for use in shock tubes, exploding environments, and other temporally changing environments.

Figure 10:
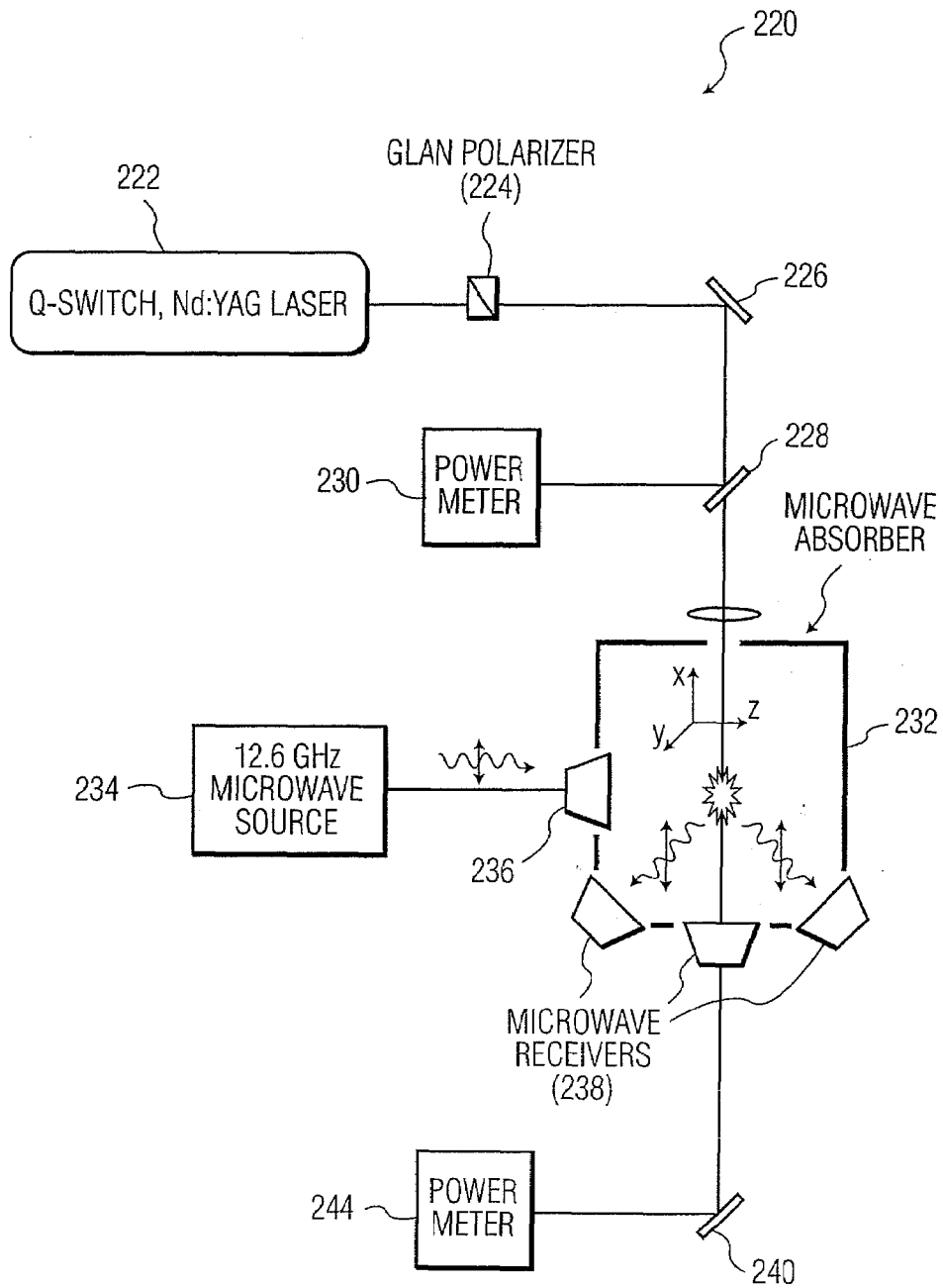
FIG. 10 is a diagram showing another experimental setup for testing the microwave detection technique of the present invention.

FIG. 10 is a diagram showing another experimental setup, indicated generally at 220, for testing the present invention. In this setup, a single laser spark was generated in air, and properties of the spark were remotely determined using microwaves. A Q-switched, frequency-doubled, Nd: YAG laser 222 (Continuum YG661-10, pulse width 8 nanoseconds) was used to generate a breakdown of the room air. One Glan-Thomson prism 224 was used to vary the power of the laser beam without changing its time characteristics. The beam was reflected by a mirror 226 and focused in the room air by a lens of 10 cm focal length. The laser focal region in the air had dimensions of about 1 mm in length and about less than 10 microns in diameter. A tunable, Gunn-diode microwave source 234 (West Divident, operating frequency: 12.6 GHz, wavelength: 2.38 cm, power: about 15 mW) was beamed into the breakdown area through a microwave horn 236 (WR75). The polarization of the microwave radiation was along the propagation direction of the laser beam. The source itself was covered by a metal box to minimize the background signal. The distance between the laser spark and the source microwave horn (WR75) was 30 cm. The microwave scattering was detected with a second horn 238 (WR75) and associated receiver (not shown), placed at three locations over time. The distance between the laser spark and the receiving horn was between 15-35 cm, which is much greater than the 2.38 cm wavelength of the microwave and very much greater than the scale of the plasma so that the far-field scattering approximation is valid. The received microwave signal was amplified by an amplifier with a gain factor 30 dB and then rectified by a diode (HP8427A). Care was taken to make sure that the whole breakdown area was surrounded by microwave absorbers 232 (>20 dB) to minimize electronic disturbances and spurious scattering that would otherwise affect the microwave scattering measurement. Power meters 230 and 244 and their respective dichroic lenses 228 and 240 allowed for measurement of laser power levels.

Figure 11:
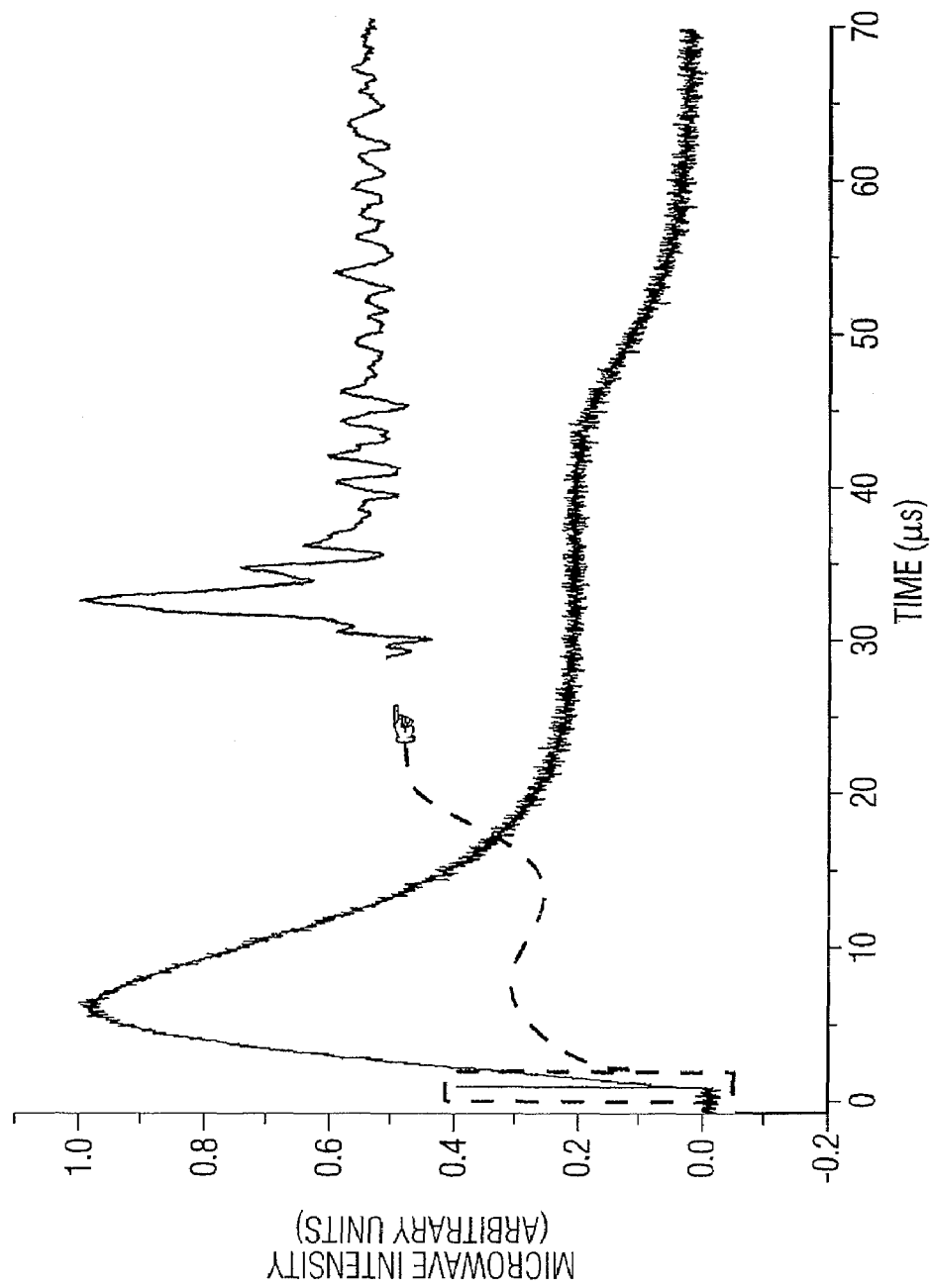
FIGS. 11-15 are graphs showing measurements generated by the experimental setup shown in FIG. 10.

FIG. 11 is a graph showing a sample microwave measurement from the laser-induced breakdown generated in the experiment depicted in FIG. 10. For this shot, the laser beam had an energy of 55 mJ, leading to strong, laser-induced ionization dominated by the avalanche ionization process. This strong avalanche ionization signal typically is composed of two features. In time sequence, the first peak occurs over an approximately 20 ns time scale and is called the "precursor" pulse. The second peak which occurs at 7.5 microseconds is the after-spark evolution of the plasma. The rising edge of the precursor pulse reveals information on the avalanche phase of the laser breakdown. The avalanche phase of the optical breakdown is only valid until thermal ionization becomes dominant, which occurs when the temperature of the plasma reaches greater than $10^4$ K. During the precursor pulse, the scale of the plasma remains small, and for the whole ionization process, the plasma region is expected to remain transparent to the microwave radiation because the skin layer thickness is projected to be greater than plasma scale. For example, even for a fully ionized laser induced air plasma, with a conductivity $\sigma \sim 10^4$ Ohm·m, at the microwave frequency used in these experiments, $\omega \approx 2\pi \cdot 12.6 \cdot 10^9$ rad/sec, the skin layer thickness ($\delta \approx 4 \cdot 10^{-5}$ m) is greater than the plasma scale ($r_0 \approx 10^{-5}$) m. When the plasma is close to a thermal, fully ionized plasma, the conductivity depends primarily on temperature $\sigma \propto T^{3/2}$. From Equation 8 above, the microwave scattering intensity $I_s \approx <\Theta> \propto \sigma^2 V_0^2 \propto T^3$ in that regime. Therefore, the scattered signal intensity increases during the laser pulse both from the avalanche ionization and the rapid temperature increase. After the laser pulse ends, cooling due to the radiation losses causes the plasma temperature and, therefore the conductivity to go down, leading to the observed decrease of the scattered precursor intensity. This explains the precursor temporal shape. The lowest point in the curve can be regarded as the transition from the precursor to the after-spark evolution. The second broad peak is related to the after spark dynamics of the plasma, including the growth of the plasma region and expansion cooling.

Figure 12:
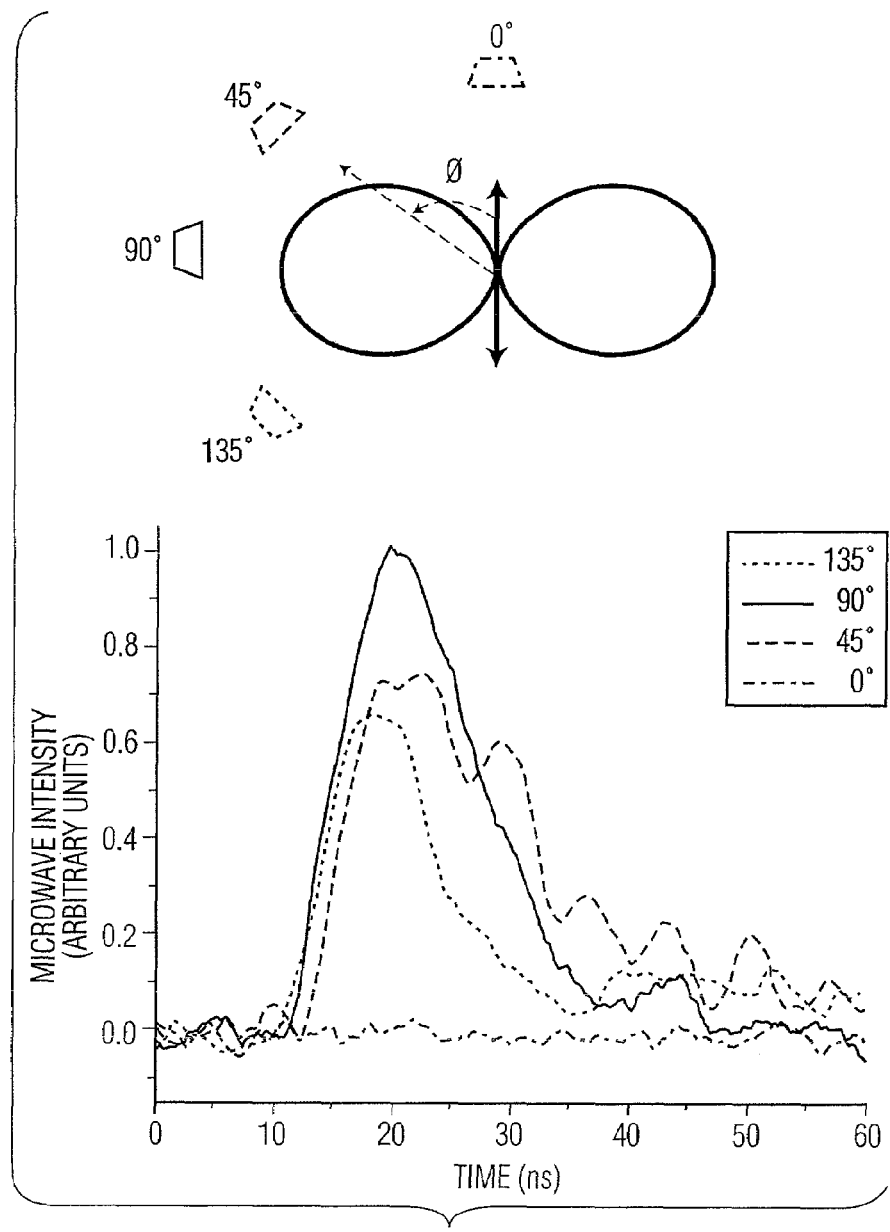
Figure 13:
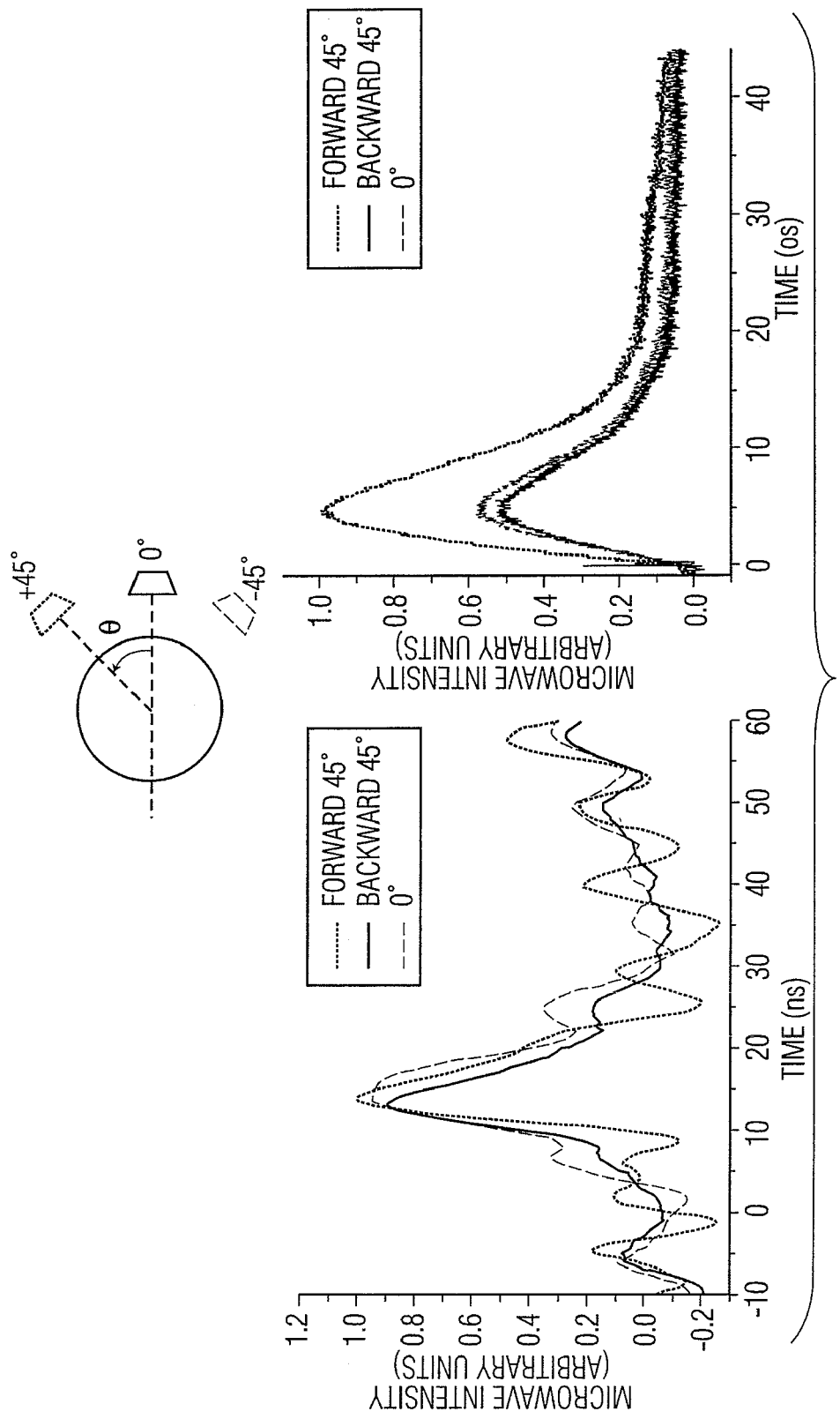

FIG. 12 shows precursor scattering at different angular positions φ of the microwave receiver 238 of FIG. 10, relative to the microwave induced polarization direction. For a point dipole, it is assumed that the induced polarization lies along the polarization direction of the applied microwave field. The data in FIG. 10 indicate that the scattered microwave has a dipole radiation pattern, with a maximum at φ=90° and 0 for φ=0°. Scattering signals from receivers at θ=45° and 135° positions show signals that are lower than the ones at 90°, as expected for a dipole scatterer. FIG. 13 shows the same precursor but in the φ=90° plane through the dipole center and normal to the polarization axis. On the right are the data from the full time evolution of the laser induced discharge, and on the left is an expanded view of the scattering from the precursor portion of that time interval. The precursor signals measured with the receiver located at θ=−45°, θ=0° and θ=+45° are almost identical, showing that during the precursor period, the scatterer is acting like an ideal dipole and the scattering is Rayleigh in nature. In the longer time regime, however, the plasma grows and moves into the Mie regime, where it is no longer symmetric about the polarization axis.

Figure 14:
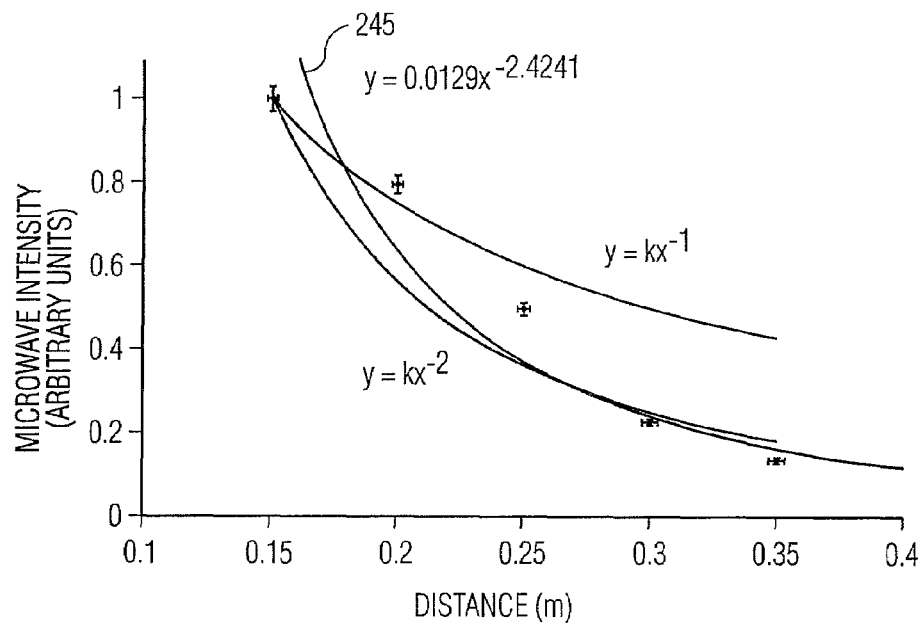

FIG. 14 is a graph showing the maximum microwave scattering intensity at different distances of the receiver from the dipole precursor scatterer at Φ=90°. The line 245 is a fit to the data. It shows that microwave scattering intensity has a square dependence of distance in the far-field and also, that the scattering from the background is small as compared with the scattering from the laser spark. If that were not the case, then interference effects with the background would cause the dependency to be oscillatory and less than the squared dependence measured.

The results shown in FIGS. 11-14 demonstrate that the received microwave signal from the precursor is consistent with microwave scattering that has a dipole radiation pattern. As such, the precursor microwave scattering signal is a direct measure of the electron number density.

Figure 15:
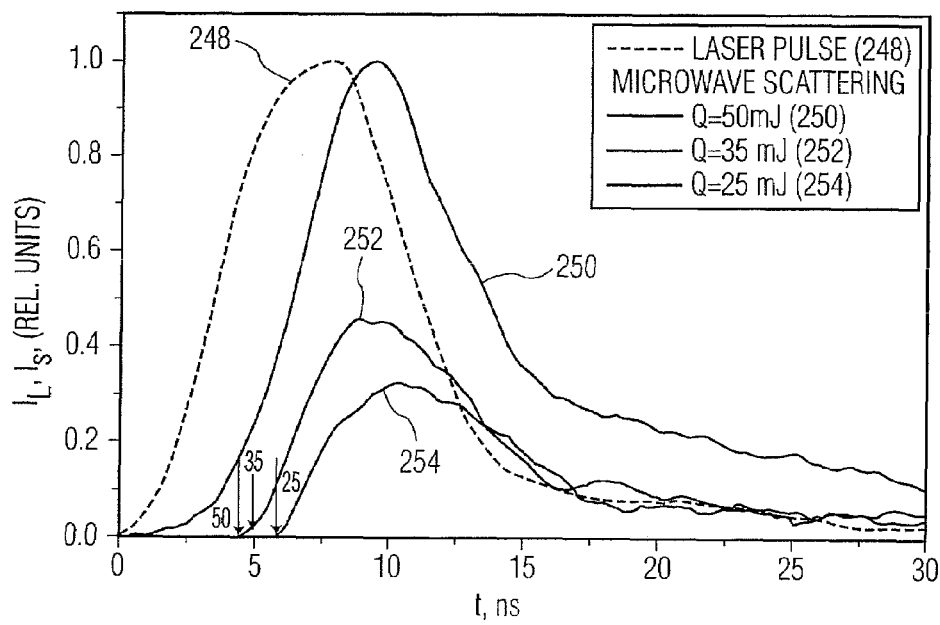
Figure 16A:
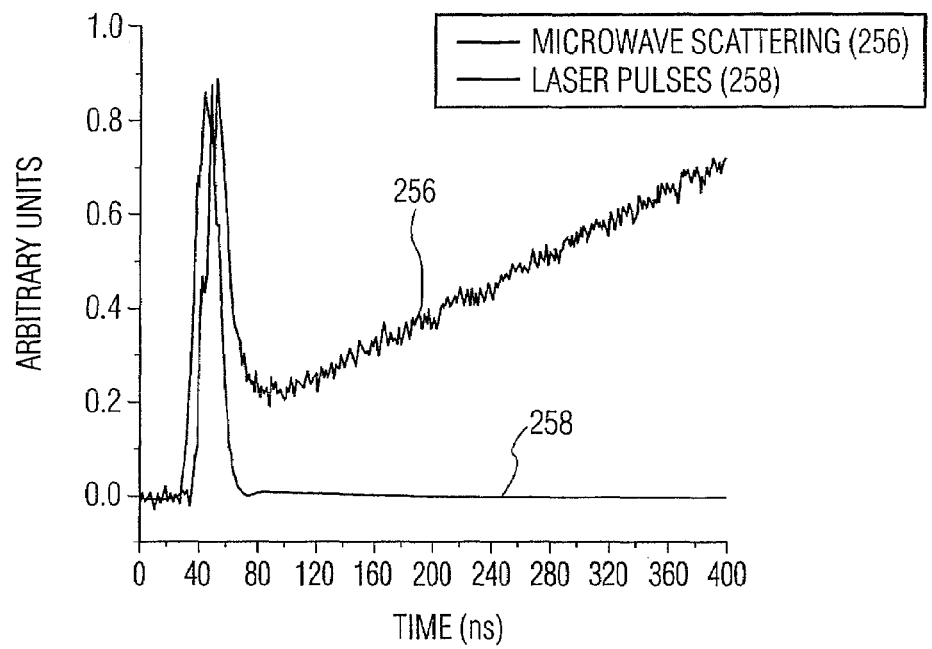
FIGS. 16A-16F show graphs of multiple, sequential laser pulses and associated microwave scattering.
Figure 16B:
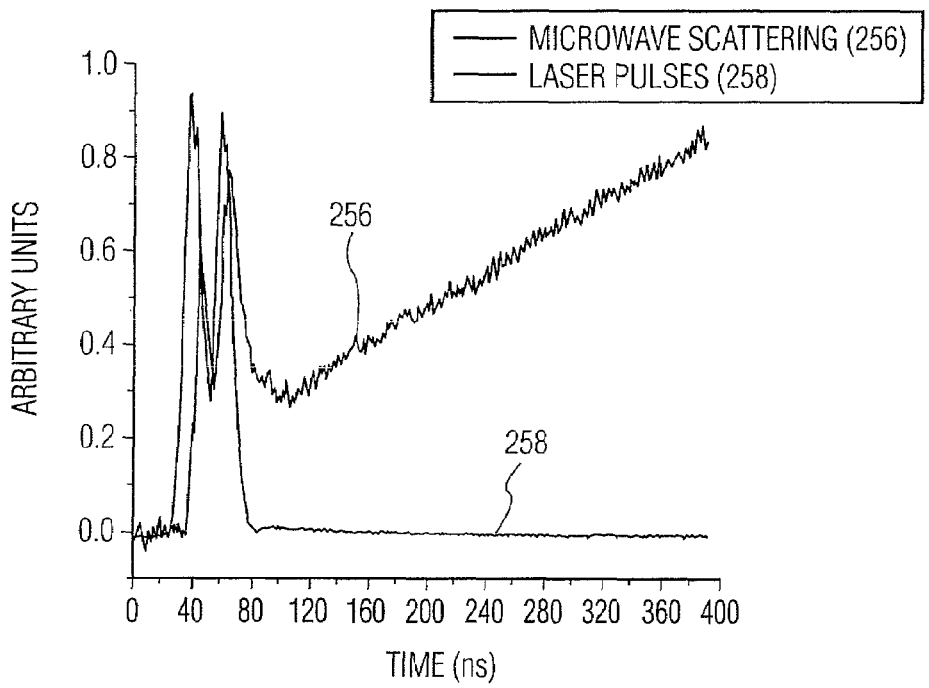
Figure 16C:
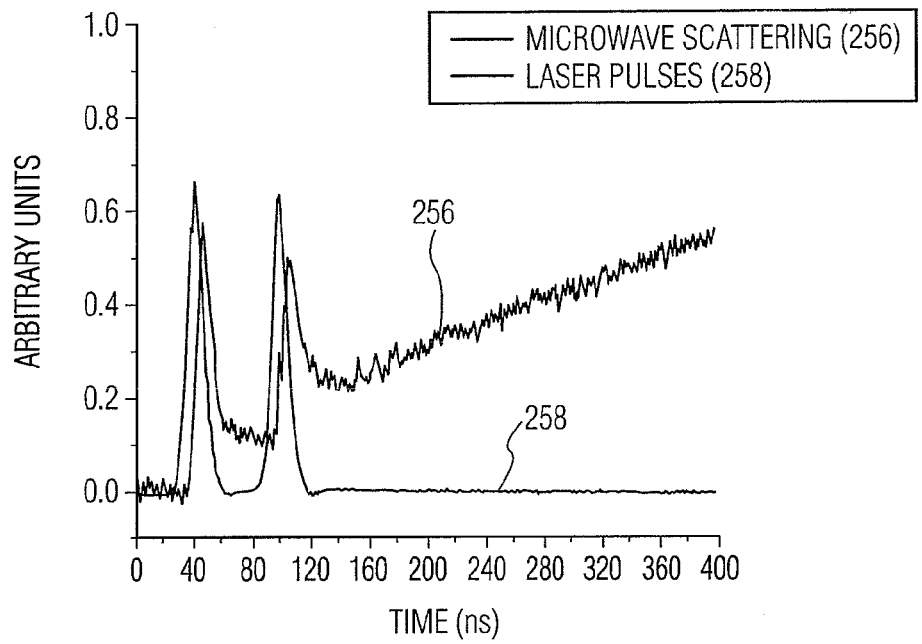
Figure 16D:
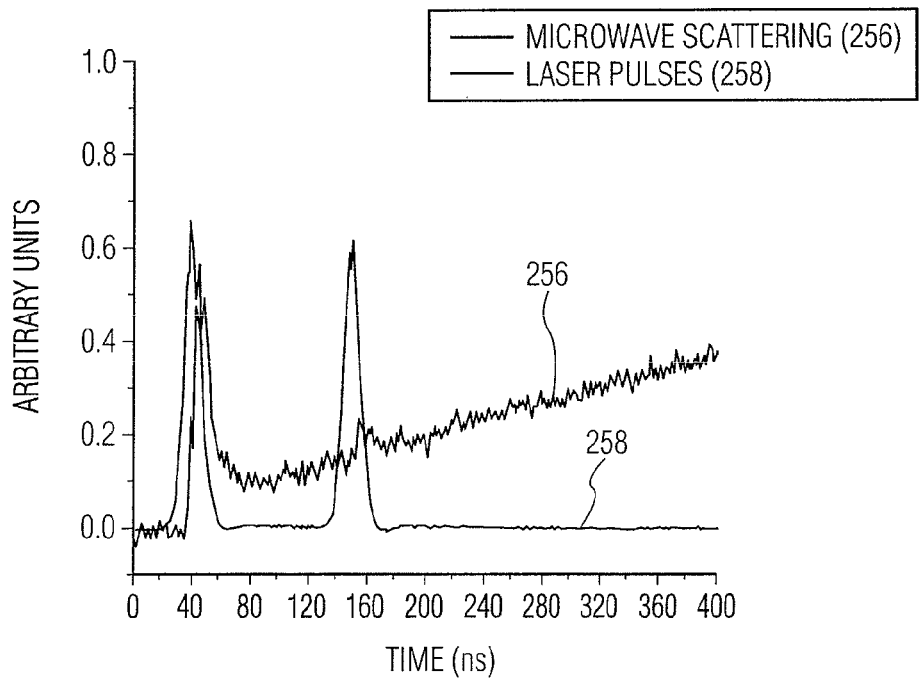
Figure 16E:
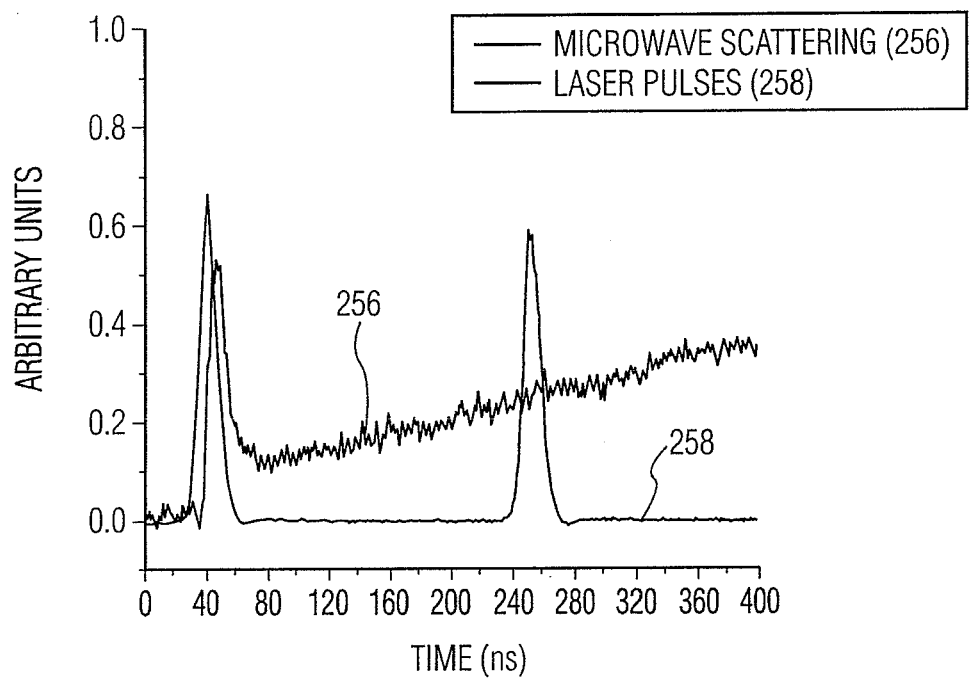
Figure 16F:
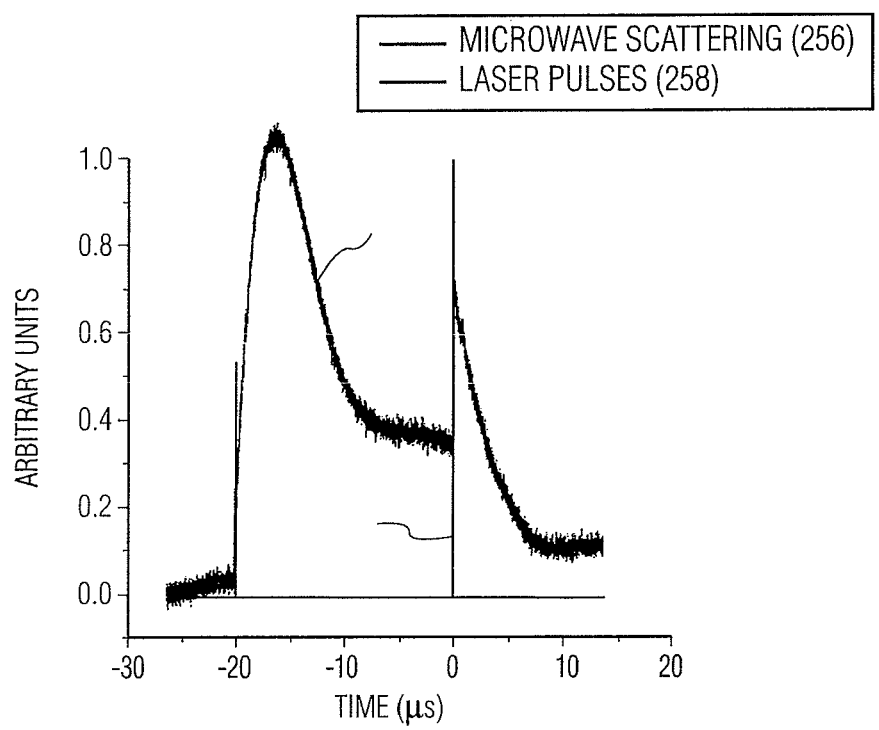

FIG. 15 is a graph showing experimental results for the scattered microwave signal versus time during the precursor pulse, obtained at different laser pulse powers. The dotted line 248 indicates the normalized laser pulse amplitude. The microwave scattering signals are normalized relative to the 50 mJ case, shown in line 250. Note that the laser shots at sequentially lower power are sequentially more delayed as expected from Equation 9. The 35 mJ and 25 mJ cases are shown in lines 252 and 254, respectively. The small arrows at the bottom indicate good agreement with predicted delays. Measuring of the scattering delay time for reaching a given scattered signal intensity can give information about the initial bulk plasma density preceding the optical breakdown.

For applications of the present invention to longer-range diagnostics, such as might be of interest for long-distance, stand-off detection, it is useful to examine the effects of using multiple pulses either for time sequenced ionization or for the creation of multiple breakdown regions. To explore the time sequencing, a double pulsed laser (both pulses have a pulse energy=40 mJ/pulse, wavelength=532 nm, pulse length=8 ns) with an adjustable time delay was used to generate sequential laser sparks in air. The microwave scattering signals from sequential laser sparks is shown in FIGS. 16A-16F. In each of the graphs, line 256 represents the microwave scattering, and line 258 represents the laser pulse. When the time delay is within a few nanoseconds, there is no detectable difference between two sparks, as shown in graph A. When the delay is about 30 nanoseconds, the second peak generated by the second laser pulse produces a stronger precursor, which corresponds to a higher electron number density, as shown in graph B. When the delay increases to greater than 60 nanoseconds but still less than the peak of the spark evolution, the second peak is lower than the first peak, as shown in graphs C-E. When the delay is longer than the 7 to 10 microseconds corresponding to the spark evolution peak, a significant increase of precursor can be seen in graph F. This may be explained by rapid cooling causing the density at the core of the plasma to increase back to almost ambient density with a residual high electron density that facilitates ionization in the plasma region.

Figure 17:
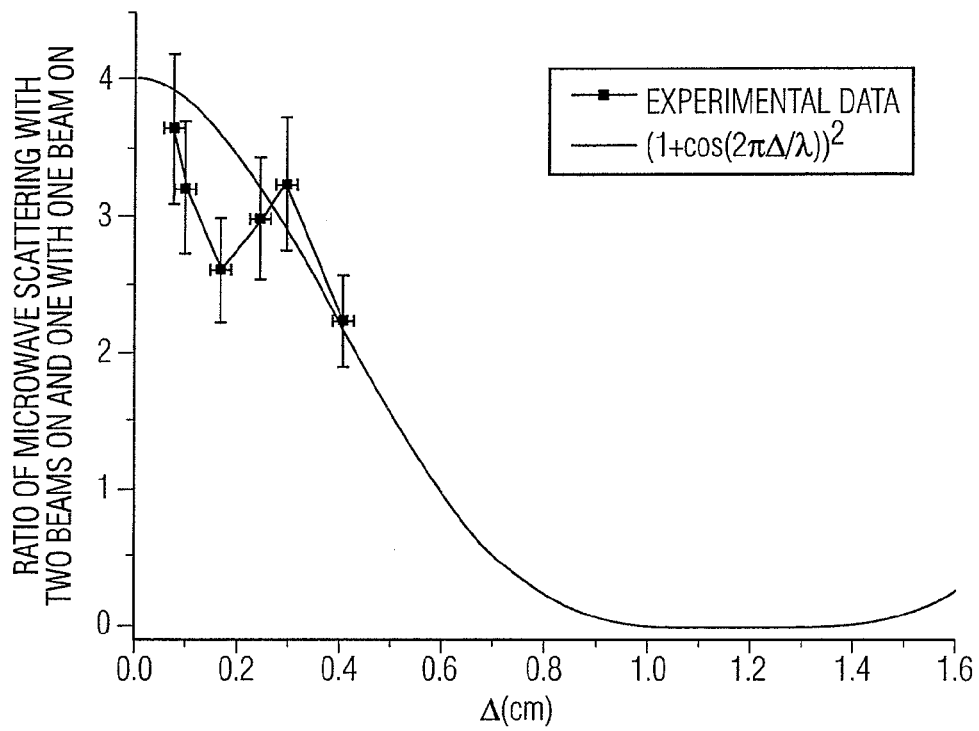
FIG. 17 is a graph showing microwave scattering for differential separations between laser sparks.

Simultaneous, double laser spark studies were conducted using a single, Nd:YAG laser output (laser pulse power=60 mJ/pulse, wavelength=532 nm, pulse length=8 ns), which was split into two beams by a 50/50 beam splitter. After focusing the two beams by two lenses with same focus length (f=5 cm), the microwave scattering signal for different separations between laser sparks was measured and is shown in FIG. 17. The curve shows the predicted intensity as a function of separation and the points show the measured values. The microwave source horn illuminated the breakdown points from the side, so that one plasma region was illuminated before the other. The receiving horn was facing the breakdown points on the plane of symmetry between the two breakdown points. The skin layer of laser sparks at the microwave frequency is always greater than the size of the plasma, so dipole scattering can be assumed. For coherent scattering, the electric fields scattered from the two sources add together. The square of the total electric field is the measured power. Thus, the peak power for two identical scatterers is four times the power measured from a single scatterer. As the separation is increased, the path length difference increases and full cancellation occurs at a separation of half the wavelength, or 1.15 cm in the case shown in FIG. 17. For incoherent scattering, the intensities add and the detected signal is twice the single intensity. It can be seen from FIG. 17 that the scattered intensity reaches four times the single spark when the separation is small and falls at close to the predicted rate for coherent scattering with separation. Thus, the microwave scattering from two laser sparks is coherent. This experimental result reveals the possibility of using microwave scattering from a series of laser-induced plasmas to enhance backward scattering.

Figure 18:
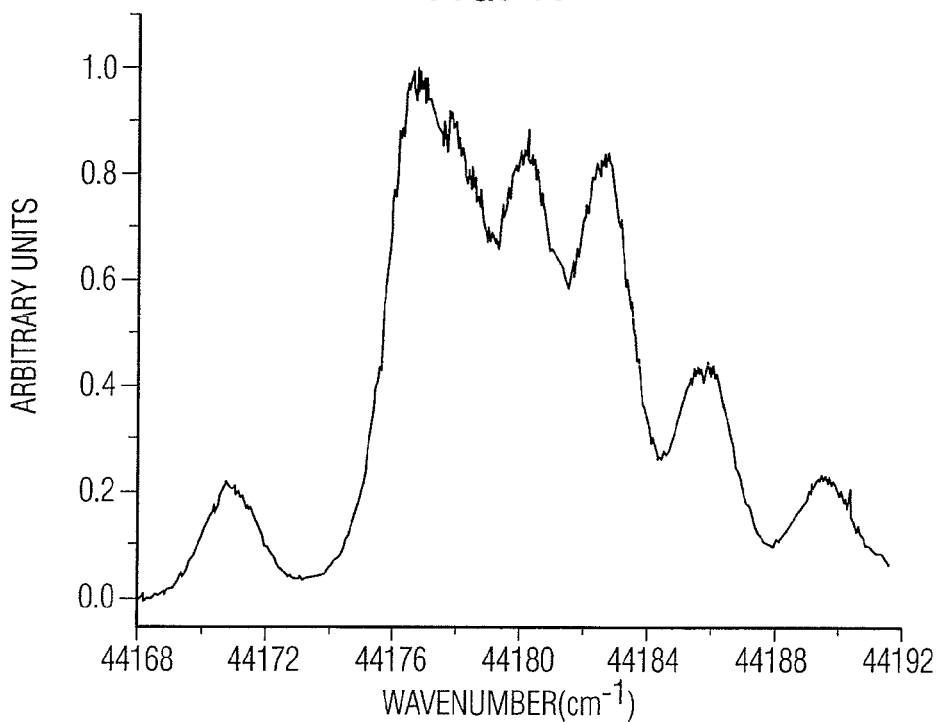
FIG. 18 is a graph showing a spectrum of nitric oxide measured using the present invention.

FIG. 18 is a graph showing a spectrum of nitric oxide measured by the present invention, using a (1+1) REMPI technique with a frequency tunable laser operating in the vicinity of 226 nm, which corresponds to a well-known single photon resonance in nitric oxide. This spectrum demonstrates the capability of the present invention to identify species and observe the spectrum of said species in order to determine parameters such as the species temperature and density.

Figure 19:
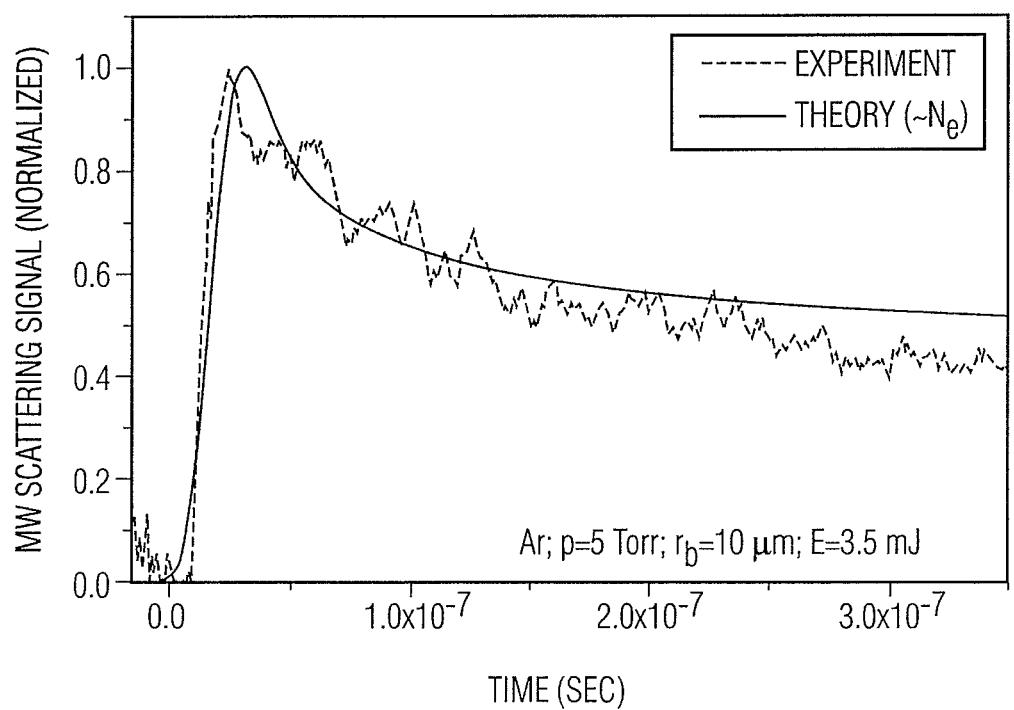
FIG. 19 is a graph illustrating the time dependence of a microwave signal generated using a (3+1) REMPI process in argon at 5 Torr, showing the electron loss rate and comparison with model predictions.

FIG. 19 is a graph illustrating the time dependence of a microwave signal generated using a (3+1) REMPI process in argon at 5 Torr, showing the electron loss rate and comparison with model predictions. The dotted and solid lines correspond, respectively, to measured and predicted microwave time dependencies generated using a 3.0 mJ laser pulse, at 261 nm, focused to a spot diameter of 10 micrometers. The time dependencies are indicative of the loss rate of the free electrons and are a function of the local temperature, density and species of the gas or plasma. By comparing the loss rate with calibration measurements and with model predictions, the present invention can be used to determine the local gas or plasma properties. Thus, the specific microwave scattering patterns received by the present invention can be used to remotely identify a property of a gas or a plasma. For example, the amplitudes of a received microwave scattering pattern can be used to remotely determine the electron loss rate of a gas or plasma. This information can then be used to remotely determine the temperature and density of the gas or plasma.

Importantly, detection by the present invention of ionization using microwave scattering eliminates the need for a local probe detector. As such, the present invention allows for remote detection in gas flows and combusting environments that are at operational pressures (including atmospheric pressure) and in large-scale devices, such as wind tunnel facilities and combustors. Additionally, the volume of plasma to be analyzed can be made very small and relatively non-perturbative, due to the sensitivity of the present invention to microwaves scattered by the plasma.

An advantage of the present invention is that velocity measurements of gases or plasmas can be precisely timed by the firing of the laser and precisely located with optical elements. Thus, the present invention can be used with pulsed facilities such as shock and expansion tubes. Further, ionization occurs as long as the laser is focused to high enough power, so there is little sensitivity to flow parameters such as temperature and species mole fractions. At low densities, the laser requires higher intensity to achieve breakdown, but nevertheless, the measurement of velocity is feasible.

The present invention is capable of measuring concentrations of species, including minor species and radicals, in the part-per-trillion range. A pulsed microwave system is used for the detection of such species. For example, the presence of NO is of importance both for combustion and in hypersonic wind tunnels, for the determination of the air quality and chemical reaction processes. When high sensitivity is achieved, the present invention is capable of detecting combustion radicals. As such, the present invention allows for the detection of pollutants and hazardous gases. Since a microwave system is used by the present invention, analysis of gas flows is extendable to long ranges with radar, which is useful for environmental monitoring. The measurement of the scattering by microwave has high sensitivity because there is very little background noise at the microwave frequency and heterodyne methods can be used for detection.

Having thus described the invention in detail, it is to be understood that the foregoing description is not intended to limit the spirit and scope thereof. What is desired to be protected by Letters Patent is set forth in the following claims.

What is claimed is:

1. An apparatus for remotely monitoring properties of gases, comprising:
   a laser for generating an ionized sample region within a gas to be monitored;
   a transmitter for transmitting electromagnetic radiation to the ionized sample region;
   a receiver for receiving scattered electromagnetic radiation from the ionized sample region; and
   an electromagnetic detection system for processing changes in the scattered electromagnetic radiation to remotely determine a property of the gas.

2. The apparatus of claim 1, wherein the electromagnetic radiation comprises microwave radiation and the scattered electromagnetic radiation comprises scattered microwave radiation.

3. The apparatus of claim 1, wherein the electromagnetic detection system processes the scattered electromagnetic radiation to establish a frequency shift between the transmitted electromagnetic radiation and the scattered electromagnetic radiation received by the receiver.

4. The apparatus of claim 3, wherein the electromagnetic detection system processes the frequency shift to determine a velocity of the gas.

5. The apparatus of claim 1, wherein the electromagnetic detection system processes the changes in the scattered electromagnetic radiation to determine a temperature of the gas.

6. The apparatus of claim 1, wherein the electromagnetic detection system processes the changes in the scattered electromagnetic radiation to determine electron losses in the gas.

7. The apparatus of claim 1, wherein the electromagnetic detection system processes the changes in the scattered electromagnetic radiation to determine a density of the gas.

8. The apparatus of claim 1, wherein the electromagnetic detection system processes the changes in the scattered electromagnetic radiation to determine a refractive index of the gas.

9. The apparatus of claim 1, wherein the ionized sample region is generated using a resonant, enhanced, multiphoton ionization process.

10. The apparatus of claim 1, wherein the electromagnetic detection system comprises a homodyne detection system.

11. The apparatus of claim 10, wherein the homodyne detection system mixes the scattered electromagnetic radiation with the transmitted electromagnetic radiation to determine a property of the gas.

12. The apparatus of claim 1, wherein the electromagnetic detection system comprises a heterodyne detection system.

13. The apparatus of claim 12, wherein the heterodyne detection system mixes the scattered electromagnetic radiation with a reference signal to determine a property of the gas.

14. The apparatus of claim 1, wherein the laser comprises a frequency-tunable laser.

15. The apparatus of claim 14, wherein the frequency of the laser is swept across a band of frequencies and the electromagnetic detection system processes the changes in the scattered electromagnetic radiation to identify at least one molecular species in the gas.

16. The apparatus of claim 14, further comprising tuning the laser through a photon resonance of an atom or a molecule so that an electron density in the ionization sample region reflects a spectrum of the atom or the molecule.

17. The apparatus of claim 1, further comprising a second electromagnetic receiver for receiving scattered electromagnetic radiation from the ionized sample region.

18. The apparatus of claim 17, wherein the electromagnetic detection system processes the scattered electromagnetic radiation to determine a two-dimensional velocity vector of the gas.

19. The apparatus of claim 17, further comprising a third electromagnetic receiver for receiving scattered electromagnetic radiation from the ionized sample region.

20. The apparatus of claim 19, wherein the electromagnetic detection system processes the scattered electromagnetic radiation to determine a three-dimensional velocity vector of the gas.

21. The apparatus of claim 1, wherein the electromagnetic detection system processes the scattered electromagnetic radiation to generate a scattering pattern.

22. The apparatus of claim 1, wherein the changes in the scattered electromagnetic radiation indicate physical properties of an ionization regime of the gas.

23. An apparatus for remotely monitoring properties of plasmas, comprising:
   a laser for generating an ionized sample region within a plasma to be monitored;
   a transmitter for transmitting electromagnetic radiation to the ionized sample region;
   a receiver for receiving scattered electromagnetic radiation from the ionized sample region; and
   an electromagnetic detection system for processing changes the scattered electromagnetic radiation to remotely determine a property of the plasma.

24. The apparatus of claim 23, wherein the electromagnetic radiation comprises microwave radiation and the scattered electromagnetic radiation comprises scattered microwave radiation.

25. The apparatus of claim 23, wherein the electromagnetic detection system processes the scattered electromagnetic radiation to establish a frequency shift between the transmitted electromagnetic radiation and the scattered electromagnetic radiation received by the receiver.

26. The apparatus of claim 25, wherein the electromagnetic detection system processes the frequency shift to determine a velocity of the plasma.

27. The apparatus of claim 23, wherein the electromagnetic detection system processes the changes in the scattered electromagnetic radiation to determine a temperature of the plasma.

28. The apparatus of claim 23, wherein the electromagnetic detection system processes the changes in the scattered electromagnetic radiation to determine electron losses in the plasma.

29. The apparatus of claim 23, wherein the electromagnetic detection system processes the changes in the scattered electromagnetic radiation pattern to determine a density of the plasma.

30. The apparatus of claim 23, wherein the electromagnetic detection system processes the changes in the scattered electromagnetic radiation to determine a refractive index of the plasma.

31. The apparatus of claim 23, wherein the ionized sample region is generated using a resonant, enhanced, multiphoton ionization process.

32. The apparatus of claim 23, wherein the electromagnetic detection system comprises a homodyne detection system.

33. The apparatus of claim 32, wherein the homodyne detection system mixes the scattered electromagnetic radiation with the transmitted electromagnetic radiation to determine a property of the plasma.

34. The apparatus of claim 23, wherein the electromagnetic detection system comprises a heterodyne detection system.

35. The apparatus of claim 34, wherein the heterodyne detection system mixes the scattered electromagnetic radiation with a reference signal to determine a property of the plasma.

36. The apparatus of claim 23, wherein the laser comprises a frequency-tunable laser.

37. The apparatus of claim 36, wherein the frequency of the laser is swept across a band of frequencies and the electromagnetic detection system processes the changes in the scattered electromagnetic radiation to identify at least one molecular species in the plasma.

38. The apparatus of claim 36, further comprising tuning the laser through a photon resonance of an atom or a molecule so that an electron density in the ionization sample region reflects a spectrum of the atom or the molecule.

39. The apparatus of claim 23, further comprising a second electromagnetic receiver for receiving scattered electromagnetic radiation from the ionized sample region.

40. The apparatus of claim 39, wherein the electromagnetic detection system processes the scattered electromagnetic radiation to determine a two-dimensional velocity vector of the plasma.

41. The apparatus of claim 39, further comprising a third electromagnetic receiver for receiving scattered electromagnetic radiation from the ionized sample region.

42. The apparatus of claim 41, wherein the electromagnetic detection system processes the scattered electromagnetic radiation to determine a three-dimensional velocity vector of the plasma.

43. The apparatus of claim 23, wherein the electromagnetic detection system processes the scattered electromagnetic radiation to generate a scattering pattern.

44. The apparatus of claim 23, wherein the changes in the scattered electromagnetic radiation indicates physical properties of an ionization regime of the plasma.

45. An method for remotely monitoring properties of gases, comprising:
   generating an ionized sample region within a gas to be monitored;
   transmitting electromagnetic radiation to the ionized sample region;
   receiving scattered electromagnetic radiation from the ionized sample region; and
   processing changes in the scattered electromagnetic radiation to determine a property of the gas.

46. The method of claim 45, wherein the step of transmitting electromagnetic radiation comprises transmitting microwave radiation, and the step of receiving scattered electromagnetic radiation comprises receiving scattered microwave radiation.

47. The method of claim 45, further comprising processing the scattered electromagnetic radiation to establish a frequency shift between the transmitted electromagnetic radiation and the scattered electromagnetic radiation, the frequency shift indicative of a velocity of the gas.

48. The method of claim 45, further comprising processing the changes in the scattered electromagnetic radiation to determine a temperature of the gas.

49. The method of claim 45, further comprising processing the changes in the scattered electromagnetic radiation to determine electron losses in the gas.

50. The method of claim 45, further comprising processing the changes in the scattered electromagnetic radiation to determine a density of the gas.

51. The method of claim 45, further comprising processing the changes in the scattered electromagnetic radiation to determine a refractive index of the gas.

52. The method of claim 45, further comprising generating the ionized sample region using a resonant, enhanced, multiphoton ionization process.

53. The method of claim 45, further comprising generating the ionized sample region using an avalanche process.

54. The method of claim 45, further comprising generating the ionized sample region using a laser.

55. The method of claim 54, further comprising generating the ionized sample region using a frequency-tunable laser.

56. The method of claim 55, further comprising tuning the laser through a photon resonance of an atom or a molecule so that an electron density in the ionization sample region reflects a spectrum of the atom or the molecule.

57. The method of claim 45, further comprising processing the changes in the scattered electromagnetic radiation to identify at least one molecular species in the gas.

58. An method for remotely monitoring properties of plasmas, comprising:
   generating an ionized sample region within a plasma to be monitored;
   transmitting electromagnetic radiation to the ionized sample region;
   receiving scattered electromagnetic radiation from the ionized sample region; and
   processing changes in the scattered electromagnetic radiation to determine a property of the plasma.

59. The method of claim 58, wherein the step of transmitting electromagnetic radiation comprises transmitting microwave radiation, and the step of receiving scattered electromagnetic radiation comprises receiving scattered microwave radiation.

60. The method of claim 58, further comprising processing the scattered electromagnetic radiation to establish a frequency shift between the transmitted electromagnetic radiation and the scattered electromagnetic radiation, the frequency shift indicative of a velocity of the plasma.

61. The method of claim 58, further comprising processing the changes in the scattered electromagnetic radiation to determine a temperature of the plasma.

62. The method of claim 58, further comprising processing the changes in the scattered electromagnetic radiation to determine electron losses in the plasma.

63. The method of claim 58, further comprising processing the changes in the scattered electromagnetic radiation to determine a density of the plasma.

64. The method of claim 58, further comprising processing the changes in the scattered electromagnetic radiation to determine a refractive index of the plasma.

65. The method of claim 58, further comprising generating the ionized sample region using a resonant, enhanced, multiphoton ionization process.

66. The method of claim 58, further comprising generating the ionized sample region using an avalanche process.

67. The method of claim 58, further comprising generating the ionized sample region using a laser.

68. The method of claim 67, further comprising generating the ionized sample region using a frequency-tunable laser.

69. The method of claim 68, further comprising tuning the laser through a photon resonance of an atom or a molecule so that an electron density in the ionization sample region reflects a spectrum of the atom or the molecule.

70. The method of claim 58, further comprising processes the changes in the scattered electromagnetic radiation to determine at least one molecular species in the plasma.

* * * * *

UNITED STATES PATENT AND TRADEMARK OFFICE
CERTIFICATE OF CORRECTION

PATENT NO. : 7,560,869 B2  
APPLICATION NO. : 11/541396  
DATED : July 14, 2009  
INVENTOR(S) : Richard B. Miles and Mikhail Shneider It is certified that error appears in the above-identified patent and that said Letters Patent is hereby corrected as shown below:

In the References Cited Section, on Page 2 of the patent, in the first column under Other Publications, in the third reference, the word "Ofice" should be deleted and replaced with the word "Office," and the word "Scientic" should be deleted and replaced with the word "Scientific."

Column 8, line 30, "ξion,O₂" should be deleted and replaced with " $\xi_{ion,O_2}$ " which shows ion, $O_2$ in subscript form.

Column 18, line 30, "An" should be deleted and replaced with "A."

Column 19, line 12, "An" should be deleted and replaced with "A."

Signed and Sealed this

Third Day of November, 2009

David J. Kappos  
*Director of the United States Patent and Trademark Office*

UNITED STATES PATENT AND TRADEMARK OFFICE
CERTIFICATE OF CORRECTION

PATENT NO.       : 7,560,869 B2                                                                 Page 1 of 1
APPLICATION NO.  : 11/541396
DATED            : July 14, 2009
INVENTOR(S)      : Miles et al.

It is certified that error appears in the above-identified patent and that said Letters Patent is hereby corrected as shown below:

Column 1, under STATEMENT OF GOVERNMENT RIGHTS, please delete lines 14 through 16 and insert --This invention was made with Government support under Grant No. F49620-03-1-0028 awarded by the U.S. Air Force, Office of Scientific Research. The Government has certain rights in this invention.--

Signed and Sealed this

Sixteenth Day of March, 2010

David J. Kappos
*Director of the United States Patent and Trademark Office*